US008821568B2

(12) United States Patent
Lyngstadaas et al.

(10) Patent No.: US 8,821,568 B2
(45) Date of Patent: Sep. 2, 2014

(54) IMPLANT MODIFIED WITH NON-HYDROXYLATED VITAMIN D PRECURSORS

(75) Inventors: Ståle Petter Lyngstadaas, Nesoddtangen (NO); Marta Monjo, Palma de Mallorca (ES); Christiane Petzold, Oslo (NO); Jan Erik Ellingsen, Bekkestau (NO)

(73) Assignee: Numat Biomedical S.L., Palma de Mallorca (ES)

( * ) Notice: Subject to any disclaimer, the term of this patent is extended or adjusted under 35 U.S.C. 154(b) by 0 days.

(21) Appl. No.: 13/558,971

(22) Filed: Jul. 26, 2012

(65) Prior Publication Data

US 2013/0017234 A1  Jan. 17, 2013

Related U.S. Application Data

(63) Continuation-in-part of application No. 12/995,132, filed as application No. PCT/EP2009/056666 on May 29, 2009, now abandoned.

(60) Provisional application No. 61/056,978, filed on May 29, 2008.

(51) Int. Cl.
*A61F 2/06* (2013.01)

(52) U.S. Cl.
USPC .......................................... 623/1.46; 623/1.15

(58) Field of Classification Search
CPC ......................................................... A61F 2/06
USPC ..................... 623/1.15, 1.46, 23.57
See application file for complete search history.

(56) References Cited

U.S. PATENT DOCUMENTS

2006/0088596 A1   4/2006  Labrecque et al.

2007/0010632 A1 *  1/2007  Kaplan et al. ................. 525/423
2007/0122477 A1 *  5/2007  Bishop et al. ................. 424/468
2007/0202149 A1    8/2007  Faucher et al.

(Continued)

FOREIGN PATENT DOCUMENTS

WO   WO 2006/098399         9/2006
WO   WO 2009/144313 A2    12/2009
WO   WO 2009/144313 A3    12/2009

OTHER PUBLICATIONS

G. Atkins et al., *Metabolism of Vitamin D3 in Human Osteoblasts: Evidence for autocrine and paracrine activities of 1X,25-dihydroxyvitamin D3*, 40 Bone 1517-1528 (2007).

(Continued)

*Primary Examiner* — Jason-Dennis Stewart
(74) *Attorney, Agent, or Firm* — Buchanan Ingersoll & Rooney PC

(57) ABSTRACT

An implant to be used as medical or dental implant, comprising a metallic or polymeric base which is covered by the vitamin D precursor cholecalciferol. The implant can be obtained by direct covering of the polymeric or metallic base with a solution comprising cholecalciferol or also covering the base with the 7-dehydrocholesterol (7-DHC), and subsequently irradiated with UV light to induce the formation of cholecalciferol. Optionally, the coating of the implant may include an antioxidant such as vitamin E. This implant enhances osseointegration in compromised patients by means of the endogenous synthesis and activity of vitamin D in hard and mineralized tissue regeneration. Furthermore, a method to obtain these implants which comprises coating the surface of the implant directly with cholecalciferol or with a specific concentration of 7-DHC and irradiated with UV light to induce the formation of cholecalciferol.

11 Claims, 20 Drawing Sheets

(56) References Cited

U.S. PATENT DOCUMENTS

| | | |
|---|---|---|
| 2007/0299512 A1 | 12/2007 | Korzuschnik et al. |
| 2008/0038307 A1 | 2/2008 | Hoffmann |
| 2008/0118544 A1 | 5/2008 | Wang |
| 2008/0234457 A1 | 9/2008 | Zhou et al. |
| 2008/0269870 A1 | 10/2008 | Ruuttu et al. |
| 2009/0024224 A1* | 1/2009 | Chen et al. .................. 623/23.72 |
| 2010/0158974 A1 | 6/2010 | Schomig et al. |

OTHER PUBLICATIONS

T. Melo et al., *Radicals Induced by Illumination of a Mixture of Unsaturated Fatty Acids With Ultraviolet Light at 77K*, 26 Magnetic Resonance in Chemistry 947-954 (1998).

M. Miyauchi et al., *Reversible Wettability Control of TiO2 Surface by Light Irradiation*, 511 Surface Science 401-407 (2002).

R. Moison et al., *Topically Applied Eicosapentaenoic Acid Protects Against Local Immunosuppression Induced by UVB Irradiation, cis-Urocanic Acid and Thymidine Dinucleotides*, 73(1) Photochemistry & Photobiology 64-70 (2001).

W. Olds et al., *In vitro-model of vitamin $D_3$ (Cholecalciferol) synthesis by UV radiation: Dose-response relationships.*, 93 Journal of Photochemistry and Photobiology B: Biology 88-93 (2008).

R. Pakala et al., *Eicosapentaenoic Acid and Docashexaenoic Acid Blk Serotonin-Induced Smooth Musc Cell Prolif,* Arter Throm Vasc Biol, (Aug. 1988).

H. Refsgaard et al., *Modifications of proteins by polyunsaturated fatty acid peroxidation products*, 97(2) Lab of BioChem. 611-616 (2000).

R. Willumeit et al., *Phospholipids as implant coatings*, 18 J. Mater Sci 367-380 (2007).

R. Yamauchi et al., *Analysis of Vitamin E and Its Oxidation Products by HPLC With Electrochemical Detection*, 37(5) Lipids 515-522, (2002).

G. Zhao et al., *High surface energy enhances cell response to titanium substrate microstructure*, Cell Response to Hydroxylated Titanium 49-58 (2005).

\* cited by examiner

SEQUENCE LISTING

<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ccgggagcag tgtgagctta                                          20

<210> SEQ ID NO 2
<211> LENGTH: 21
<212> TYPE: DNA
<213> ORGANISM: Artificial Sequence

```
<220> FEATURE:
<223> OTHER INFORMATION: Primer

<400> SEQUENCE: 2
tagatgcgtt tgtaggcggt c                                              21

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
agagcatgac cgatggattc                                                20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ccttcttgag gttgccagtc                                                20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
acttccatcc agttgccttc                                                20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tttccacgat ttcccagaga                                                20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
aacccagaca caagcattcc                                                20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
gagagcgaag ggtcagtcag                                                20
```

```
<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
gctccacaaa cgagaaaagc                                                   20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
agcaagggga aaaggacact                                                   20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
actggctagg tggtggtcag                                                   20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
ggtagggagc tgggttaagg                                                   20

<210> SEQ ID NO 13
<211> LENGTH: 18
<212> TYPE: DNA
<213> ORGANISM: Artificial Sequence
<220> FEATURE:
<223> OTHER INFORMATION: Primer

<400> SEQUENCE: 13
ggccacagcg cttctcag                                                     18

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
tgactttatg ggaacccgat                                                   20

<210> SEQ ID NO 15
<211> LENGTH: 20
<212> TYPE: DNA
<213> ORGANISM: Artificial Sequence
<220> FEATURE:
<223> OTHER INFORMATION: Primer
```

<400> SEQUENCE: 15
agaccatgag gttcctgcac                                                    20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
aaacagccca gtgaccattc                                                    20

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
cgtcctctgc tgccctttg gaag                                                24

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
gtgtgttgga tgtcgtgtcc accc                                               24

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
tcctgtgccc acccccatgg                                                    20

<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
agggagacta gcgtatcttg ggga                                               24

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
ctatcgggac catcgcaacg aagc                                               24

<210> SEQ ID NO 22

```
<211> LENGTH: 26
<212> TYPE: DNA
<213> ORGANISM: Artificial Sequence
<220> FEATURE:
<223> OTHER INFORMATION: Primer

<400> SEQUENCE: 22
gccccataaa atcagccaag acctca                                          26

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
acccagaaga ctgtggatgg                                                 20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
cacattgggg gtaggaacac                                                 20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
gtaacccgtt gaaccccatt                                                 20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
ccatccaatc ggtagtagcg                                                 20
```

IMPLANT MODIFIED WITH NON-HYDROXYLATED VITAMIN D PRECURSORS

CROSS-REFERENCE TO RELATED APPLICATIONS

This application claims priority to and is a Continuation-In-Part of U.S. patent application Ser. No. 12/995,132, filed on Nov. 29, 2010, which is a U.S. National Phase pursuant to 35 U.S.C. §371 of International Application PCT/EP2009/056666, filed on May 29, 2009, and published as WO 2009/144313 on Dec. 3, 2009, which claims priority to U.S. Provisional Patent Application Ser. No. 61/056,978, filed on May 29, 2008, all of which are incorporated herein by reference in their entireties for all purposes.

FIELD OF THE INVENTION

The present invention pertains to an implant to be used as a medical or dental implant, comprising a metallic or polymeric base which is covered by cholecalciferol ($D_3$). The implant can be obtained by covering the base directly with a solution of cholecalciferol or indirectly by covering said base with the vitamin D precursor 7-dehydrocholesterol (7-DHC), and subsequently irradiating it with UV light to induce the formation of cholecalciferol. This implant enhances osseointegration in compromised patients by means of the endogenous synthesis and activity of vitamin D in hard and mineralized tissue regeneration. The coating of said implant may also include an amount of an antioxidant such as vitamin E. Therefore, the present invention belongs to the field of biomaterials.

BACKGROUND OF THE INVENTION

Among the numerous functions attributed to vitamin D, current evidence suggests that its primary function is to facilitate the processes that are essential for the maintenance of a healthy and mineralized skeleton. This hormone plays a key role in calcium and phosphate homeostasis and a deficiency would lead to resorption of bone, osteoporosis, and reduced bone mineralization. In this way, this vitamin has been linked to many bone diseases, including osteoporotic hip fractures. Moreover, vitamin D improves bone mineralization in patients with chronic renal failure, supporting the fact that vitamin D directly promotes bone mineralization. Other different effects of vitamin D have been defined as anticancer and also having immunomodulatory actions. However, the use of the active vitamin D could not be applied in bone repair because of its detrimental hypercalcaemic action and toxicity.

It is well established that ultraviolet irradiation is the major source of vitamin D synthesis in the skin. 7-Dehydrocholesterol (7-DHC) is a photolabile cholesterol precursor that is converted to precholecalciferol (previtamin $D_3$) when exposed to ultraviolet B sunlight. The latter is transformed into cholecalciferol ($D_3$) and transported to the liver where is hydroxylated at carbon 25 on the side chain by vitamin $D_3$ 25-hydroxylase (CYP27A1) to form the major circulating intermediary, 25-hydroxyvitamin $D_3$ (25-$D_3$). Renal hydroxylation by 25-hydroxyvitamin $D_3$-1alpha-hydroxylase (CYP27B1) transforms the previous form into the biologically active steroid hormone, 1,25-dihydroxyvitamin $D_3$ (1,25-$D_3$) that is released to the circulation.

It is well known that human skin cells exposed to ultraviolet B (UVB) radiation (spectral range 290-315 nm) convert 7-DHC into previtamin $D_3$ in vivo and in vitro. A UVB wavelength-dependent synthesis of vitamin $D_3$ was found in these cells, showing a maximum 1,25-$D_3$ ratio formation at 302 nm and no vitamin $D_3$ production when UV wavelengths >315 nm were used (Lehman et al. UVB-induced conversion of 7-dehydrocholesterol to 1α,25-dihydroxyvitamin $D_3$ in an in vitro human skin equivalent model. Journal of Investigative Dermatology 2001; 117:1179-85). However, there is no study supporting the same activity for osteoblastic cells with 7-DHC.

Osseointegration refers to a direct structural and functional connection between living bone cells and the surface of a load-bearing implant. Titanium (Ti) is the material most commonly used for bone implants as it has outstanding physical and biological properties, such as low density, high mechanical strength, and good corrosion resistance. Current dental implant research aims at the production of innovative surfaces able to promote a more favorable biological response to the implant material at the bone-implant interface and to accelerate osseointegration. Surface preparations, chemical composition or coatings are procedures that may affect the stability of the bone-to-metal interface.

DETAILED DESCRIPTION OF THE INVENTION

The inventors of the present invention have surprisingly found that implants covered with cholecalciferol, both obtained by covering a base implant with a solution of cholecalciferol or covering the base with a solution of 7-DHC and subsequently irradiated with UV light, enhances osseointegration in hard and/or mineralized tissue. The implants of the invention have a stimulatory effect on bone cells and accelerate bone regeneration as result of endogenous synthesis of the active vitamin D by osteoblasts from its precursor cholecalciferol. The coating with non-hydroxylated vitamin D precursors shows several advantages compared to using other hydroxylated forms of vitamin D such the lower toxicity, since non-hydroxylated precursors have much lower affinity for the vitamin D receptor, which mediates the biological activity of the 1,25-$D_3$, and therefore reduces the risk of vitamin D toxicity in the target cells. The direct use of UV-irradiated 7-DHC on implants for bone regeneration purposes and increased osseointegration has never been reported before, as 7-DHC is not normally detectable in tissues and fluids of human beings except in skin. With the present invention, this problem of the toxicity of vitamin D has been solved with the use of the UV-activated vitamin D precursor, 7-DHC, and the direct use of cholecalciferol, and can now be applied for bone repair purposes to enhance osseointegration.

As shown in the Examples, osteoblasts are capable of converting cholecalciferol, both directly impregnated or from UV-photoactivated 7-DHC, into active vitamin D by expressing the enzymes required to synthesize the hydroxylated form of vitamin D, 1,25-$D_3$. Moreover, by using the method of coating the base surface of the implant with a specific concentration of 7-DHC and irradiated with UV light, the osteoblast respond with a dose-dependent increase in the enzymes required for the synthesis of the active 1,25-$D_3$, suggesting a substrate induction of its expression. When using combinations of 7-DHC with vitamin E as shown in the examples, a more efficient conversion from 7-DHC to cholecalciferol after UV-irradiation is produced, not by doing the expected function to prevent its oxidation (since the remaining amount of 7-DHC after UV-irradiation was the same as the initial) but by enhancing its conversion rate, showing then an unexpected interaction of 7-DHC with vitamin E when given together on the surface of the implants.
}

In a first aspect, the invention relates to an implant comprising a metallic or polymeric base partially or totally coated with cholecalciferol.

In another embodiment, this implant has been obtained by covering the metallic or polymeric base with a solution of 7-DHC and subsequently irradiating it with ultraviolet light to induce the formation of cholecalciferol.

In the present context, the term "implant" includes within its scope any device intended to be implanted into the body of a vertebrate animal, in particular a mammal such as a human. Non-limiting examples of such devices are medical devices that replace anatomy or restore a function of the body such as the femoral hip joint; the femoral head; acetabuiar cup; vascular stents, elbow including stems, wedges, articular inserts; knee, including the femoral and tibial components, stem, wedges, articular inserts or patellar components; shoulders including stem and head; wrist; ankles; hand; fingers; toes; vertebrae; spinal discs; artificial joints; dental implants; ossiculoplastic implants; middle ear implants including incus, malleus, stages, incus-stapes, malleus-incus, malleus-incus-stapes; cochlear implants; orthopedic fixation devices such as nails, screws, staples and plates; heart valves; pacemakers; catheters; vessels; space filling implants; implants for retention of hearing aids; implants for external fixation; and also intrauterine devices (IUDs); and bioelectronic devices such as intracochlear or intracranial electronic devices. Medical implants may also be denoted as medical prosthetic devices. Generally, a medical implant is composed of one or several implant parts.

In the present context, the term "orthopedic implant" includes within its scope any device intended to be implanted into the body of a vertebrate animal, in particular a mammal such as a human, for preservation and restoration of the function of the musculoskeletal system, particularly joints and bones, including the alleviation of pain in these structures.

In the present context, the term "dental implant" includes within its scope any device intended to be implanted into the oral cavity of a vertebrate animal, in particular a mammal such as a human, in tooth restoration procedures. Dental implants may also be denoted as dental prosthetic devices. Generally, a dental implant is composed of one or several implant parts. For instance, a dental implant usually comprises a dental fixture coupled to secondary implant parts, such as an abutment and/or a dental restoration such as a crown, bridge or denture. However, any device, such as a dental fixture, intended for implantation may alone be referred to as an implant even if other parts are to be connected thereto. Dental implants are presently preferred embodiments.

Certain preferred embodiments improve the osseointegration of implants; i.e., they improve tissue adherence to an implant, improve bone remodeling, and/or improve contact between tissues or tissues and implants. The term "osseointegration" as mentioned herein, refers to a characteristic of an implant according to the invention which refers to the direct structural and functional connection between living tissue and the surface of said implant without growth of fibrous tissue at or on the tissue-implant interface. It is not enough to improve bone growth in the vicinity of the implant, if a direct connection between the implant and the new bone does not exist. The term "hard and/or mineralized tissue" is in the present context employed to describe a variety of different naturally occurring tissue types that have become mineralized, and/or tissue having a firm intercellular substance. A hard and/or mineralized tissue according to the present invention is preferably selected from the group consisting of cartilage, bone, dental enamel, dentine-like tissue, dental hard tissue, and cortical tissue.

In a preferred embodiment, the implant comprises at least 90% by weight of a metal material. When an implant comprising one or more metal(s), metal alloy(s), and/or metal oxide(s) is referred to, this can also refer to an implant which comprises one or more additional biocompatible material(s), such as synthetic or plastic material(s). The metal, metal alloy, and/or metal oxide surface may be added on to an implant when the implant per se is made from another material or when the implant is partly made of metal, metal alloy, and/or metal oxide. This is all referred to as an implant comprising a metal, metal alloy, and/or metal oxide. Said implant can also be a graft material, preferably a metal oxide scaffold comprising titanium oxide.

The metal material may be titanium or an alloy thereof, e.g., an alloy with zirconium, tantalum, hafnium, niobium, aluminum, vanadium, chrome, cobalt, magnesium, iron, gold, silver, copper, mercury, in or zinc, and stainless steel. In a particularly preferred embodiment, the metal material is titanium.

Also, preferably the metal material is zirconium, hafnium, tantalum, niobium, or mixtures of two or more of these. The metal material preferably also is a metal hydride, such as TiH, metal hydroxide, such as TiOH, a hydride of an alloy, or a hydroxide of an alloy. Alternatively the material may be an oxide of a metal, such as metal oxide. Also, the implant material may be aluminium, gold, or surgical steel nickel.

The term "cp" is well known to the person skilled in the art and stands for "commercially pure" and relates to the level of pureness of the employed metal, such as Ti.

When the metal material is an alloy of titanium, zirconium, tantalum, hafnium, or niobium, it may be an alloy between one or more of these metal elements; or it may be an alloy containing one or more other metals such as aluminium, vanadium, chrome, cobalt, magnesium, iron, gold, silver, copper, mercury, in or zinc; or both.

In a preferred embodiment, the base of the implant comprises at least 90% by weight of titanium and/or an alloy of titanium.

In another preferred embodiment, the base of the implant comprises a polymer compatible with tissues and typically used in medical devices, particularly, polystyrene, polyurethane, or combinations thereof.

The implant described may further comprise an antioxidant, selected from, but not limited to, a vitamin E compound, vitamin C, vitamin A, lycopene, lutein, beta-carotene, alpha-carotene, zeaxanthin, selenium, zinc, coenzyme-Q10, catechins, resveratrol, proanthocyanidins, genistein, and daidzein.

The vitamin E compound comprises one or more of alpha-tocopherol, beta-tocopherol, delta-tocopherol, gamma-tocopherol, alpha-tocotrienol, beta-tocotrienol, delta-tocotrienol, gamma-tocotrienol, alpha-tocopherol acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta-tocotrienol succinate, delta-tocotrienol succinate, gamma-tocotrienol succinate, vitamin E TPGS, mixed tocopherols, derivatives, analogs, and pharmaceutically acceptable salts thereof.

Another aspect of the invention is a method for manufacturing an implant with an improved effect on adhesion of mineralized and/or hard tissue to the implant, comprising covering a metallic or polymeric base with a solution comprising cholecalciferol. In a preferred embodiment, the concentration of cholecalciferol in the coating is between 1 fmol/mm² and 5 nmol/mm². In a more preferred embodiment, the concentration of cholecalciferol in the coating is between 0.1 and 5 pmol/mm².

Another aspect of the invention is a method for manufacturing an implant with an improved effect on adhesion of mineralized and/or hard tissue to the implant, comprising the following steps:
 a) treating the metallic or polymeric base of the implant with a solution comprising 7-DHC; and
 b) irradiating at least part of the surface of the coated base of the implant with UV light for at least 30 seconds.

In the case of irradiated implants, the conversion of 7-DHC into cholecalciferol is partial, so that the final coating comprises a mixture of cholecalciferol, 7-DHC, as well as other by products such as lumisterol. The conversion achieved can be from 10 to 80%. The solvent of the solution of step a) comprising 7-DHC is typically, but not limited to, an alcohol, preferably ethanol. Once said solution is applied to the surface of the metallic or polymeric base, the solvents evaporates after some minutes and the concentration of 7-DHC in the coating is between 0.01 pmol/mm² and 10 nmol/mm². In a more preferred embodiment, the concentration of 7-DHC in the coating is between 1 and 25 pmol/mm².

In a preferred embodiment, the surface coating with UV-irradiated 7-DHC or cholecalciferol further comprises a cleaning procedure before the coating. This procedure comprises typically the implant being mechanically pre-treated by polishing or electro-polishing, sandblasting, acid-etching, plasma spraying, and/or nanostructuring, to modify the surface structure if desired, and subsequently being thoroughly cleaned using hot caustic soda followed by a degreasing step, e.g., in concentrated trichloroethylene, ethanol, or methanol, before being treated in a pickling solution, e.g., hydrofluoric acid, to remove oxides and impurities on the surface. After pickling the implant specimen is washed thoroughly in hot, double distilled, ion-exchanged water. To produce sterile devices incorporating 7-DHC or cholecalciferol with or without vitamin E, the process for producing the devices can be run under sterile conditions, or the modified implant can alternatively be sterilized after completion of the process. A post-process sterilization can be carried out by any of the methods well known for sterilization purposes in the field of medical devices and implants. Such methods typically involve autoclaving, heating, exposure to UV or ionizing radiation, or chemical sterilisation with ethylene oxide or similar chemicals.

The method also comprises the treatment of the base of the implant with a solution comprising 7-DHC which may contain or not other antioxidants such us vitamin E, followed by irradiating at least part of the surface of the coated base of the implant with UV light for at least 30 seconds and until 48 hours. In a preferred embodiment, the time of irradiation is between 15 and 60 minutes.

In a preferred embodiment, the invention thus relates to a method for manufacturing a metal implant with an improved effect on adhesion of mineralized and/or hard tissue to the implant, wherein the surface is irradiated with UV-light in the range of 250-350 nm. In a more preferred embodiment, the UV light used is between 260 and 315 nm.

In another preferred embodiment, the invention further relates to a method for manufacturing a metal implant with an improved effect on adhesion of mineralized and/or hard tissue to the implant, wherein intensity of the UV light which the surface is irradiated with is approximately 6 mW/cm².

FIGURES

Figure 4:
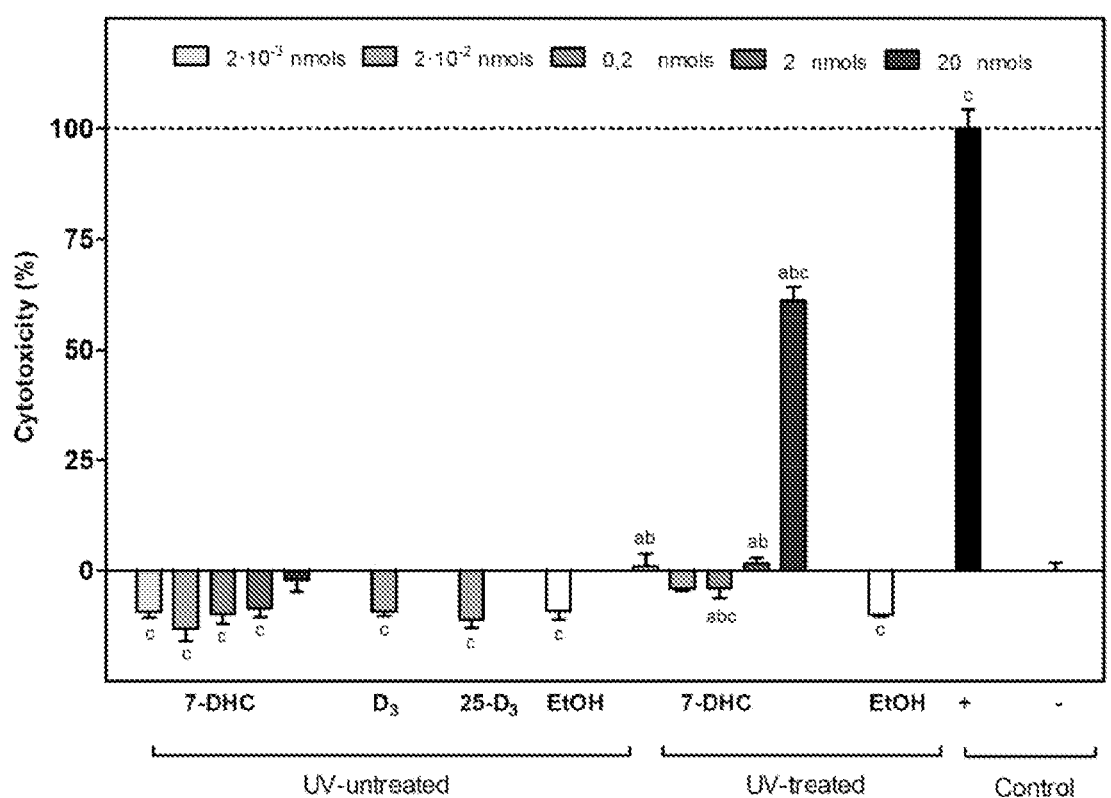

FIG. 4 shows LDH activity measured in culture media of MC3T3-E1 cells collected after 24 hours of seeding. Positive control (+; 100% toxicity) was cell culture media from cells incubated with Triton X-100 at 1%. Negative control (−; 0% toxicity) was cell culture media from control cells. Values represent the mean±SEM (N=6). Student's t-test ($p<0.05$): $^a$7-DHC UV-treated vs the corresponding 7-DHC UV-untreated; $^b$treatment vs the corresponding EtOH control and $^c$treatment vs the negative control.

Figure 5:
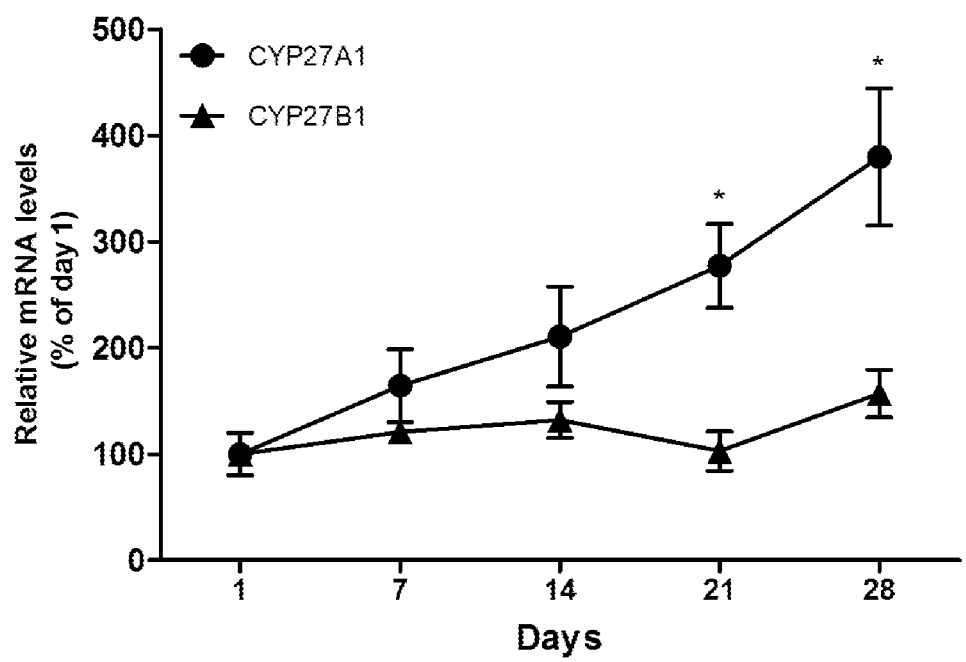

FIG. 5 shows the temporal gene expression profile of the enzymes responsible of vitamin D hydroxylation (CYP27A1, CYP27B1) in differentiating MC3T3-E1 cells. Data represent fold changes of target genes normalized to reference genes (GAPDH, 18S rRNA), expressed relative to the first day that was set at 100%. Values represent the mean±SEM (N=3). Student's t-test ($p<0.05$): *CYP27A1 mRNA expression compared to the first day of cell culture.

Figure 6:
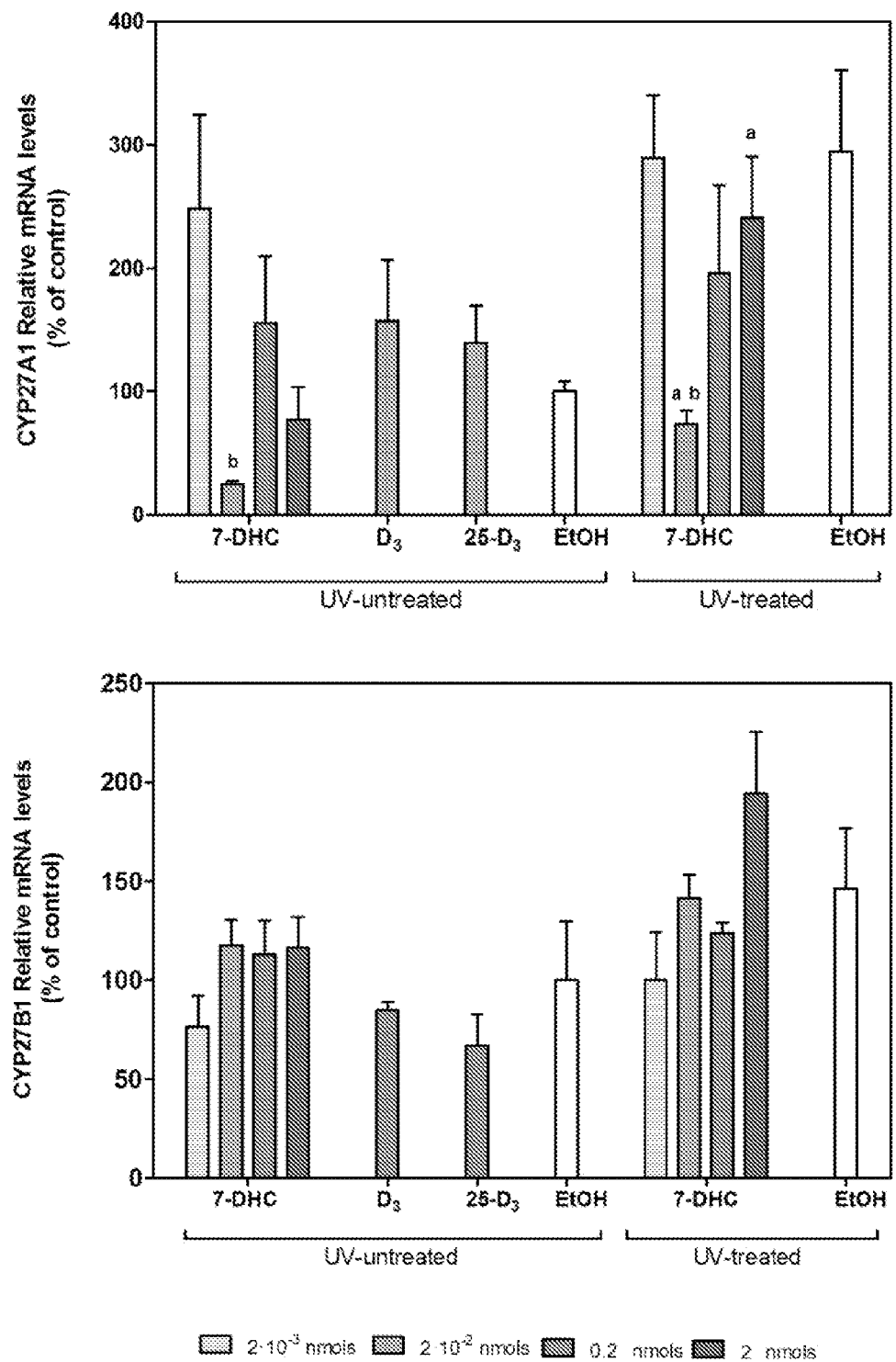

FIG. 6 shows the effect of the different treatments on gene expression levels of CYP27A1 and CYP27B1 in MC3T3-E1 cells cultured for 2 days. Data represent fold changes of target genes normalized to reference genes (GAPDH, 18S rRNA), expressed as a percentage of the EtOH UV-untreated group, which was set to 100%. Values represent the mean±SEM (N=6). Student's t-test ($p<0.05$): $^a$7-DHC UV-treated vs the corresponding 7-DHC UV-untreated and $^b$treatment vs the corresponding EtOH control.

Figure 7:
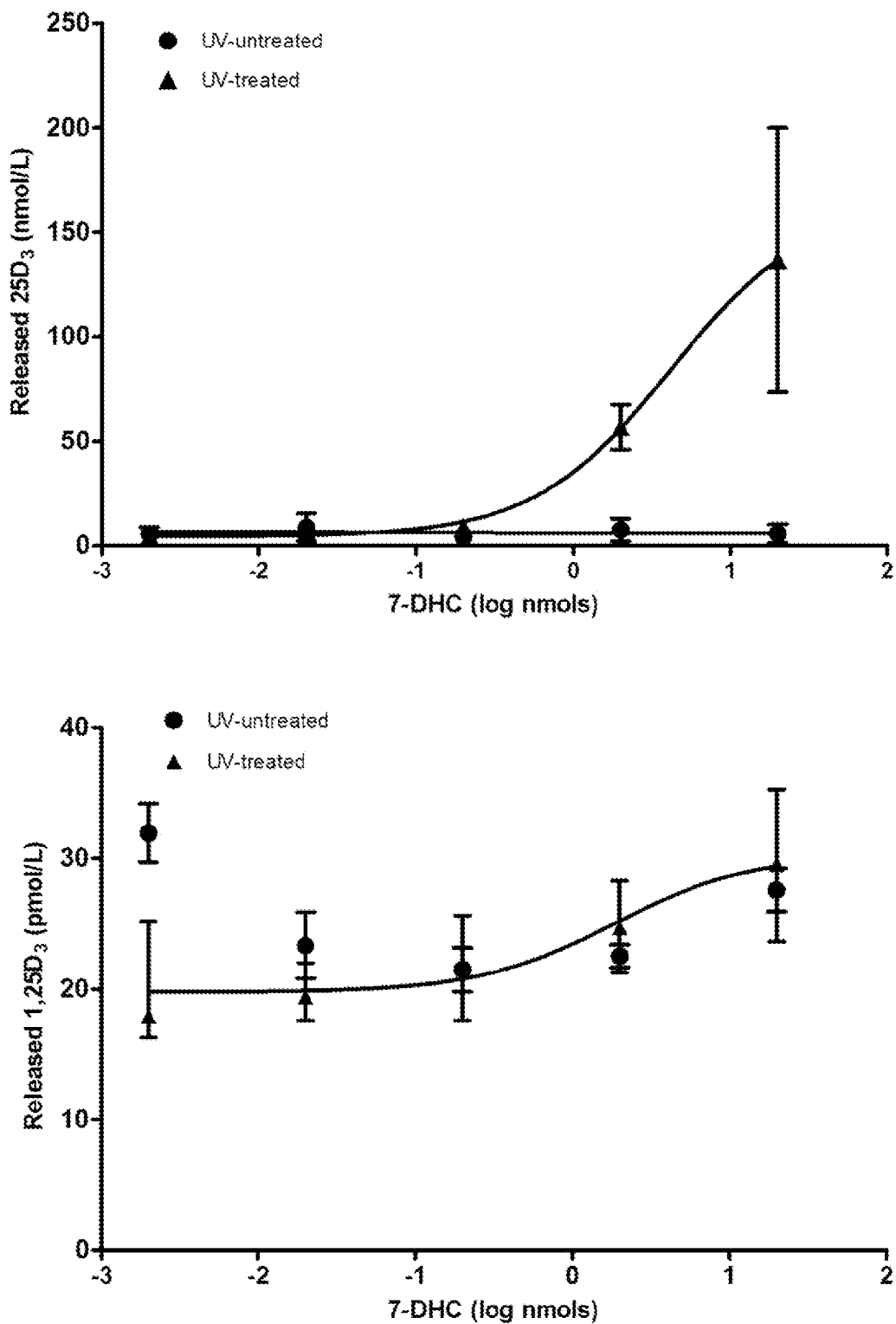

FIG. 7 shows released $25$-$D_3$ and $1,25$-$D_3$ interemediaries to the cell culture media in response to different concentrations of 7-DHC UV-treated and UV-untreated. MC3T3-E1 cells were cultured for 48 h in the presence of 7-DHC at different concentrations (20 nmols, 2 nmols, 0.2 nmols, $2\times10^{-2}$ nmols, and $2\times10^{-3}$ nmols) either UV-treated or UV-untreated. Values represent the mean±SEM (N=6). Dose-response curves were fitted with nonlinear regression analysis. Only UV-treated 7-DHC converged a dose-response curved of released $25$-$D_3$ and $1,25$-$D_3$.

Figure 8:
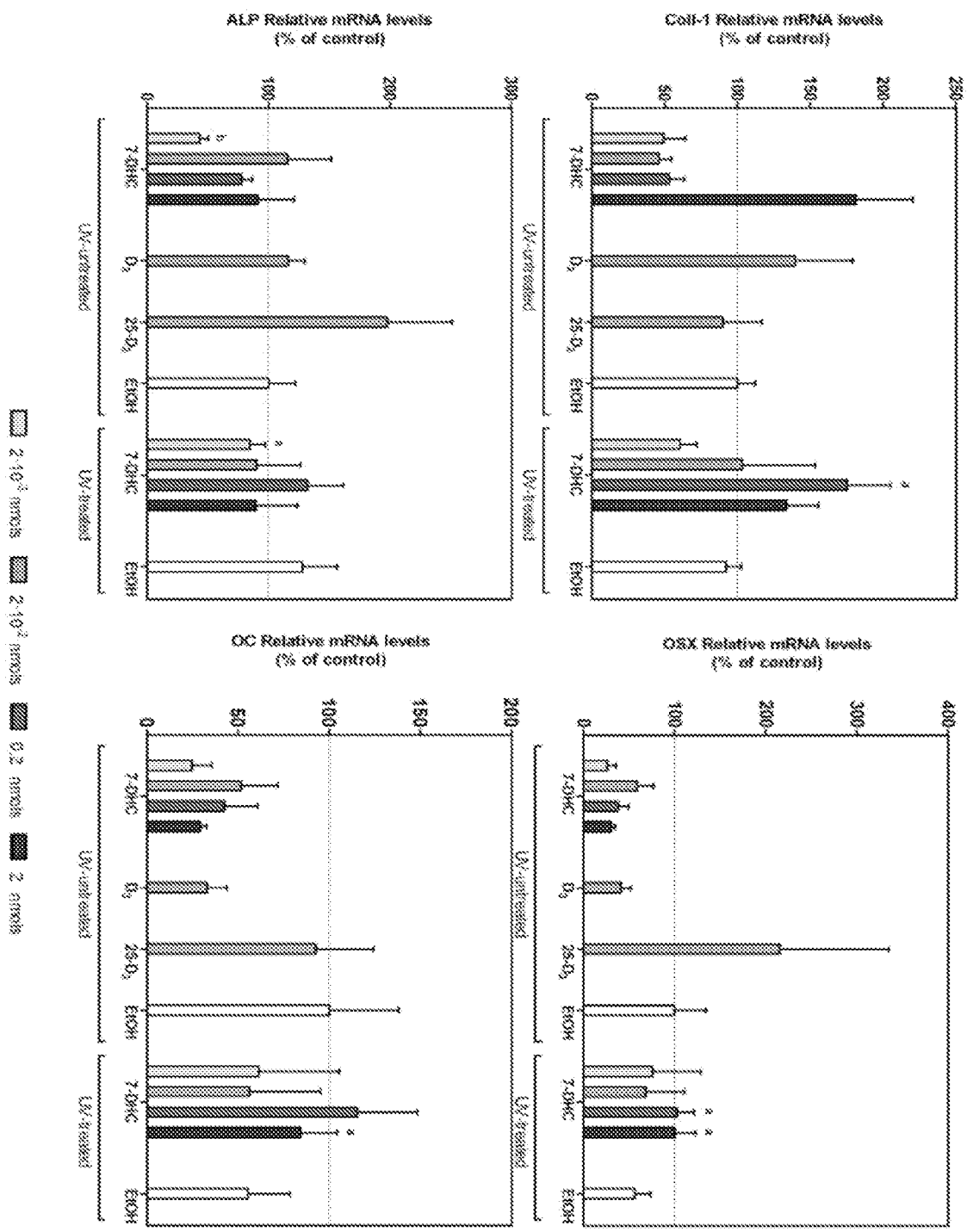

FIG. 8 shows the effect of the different treatments on gene expression levels of bone markers (Coll-1, OSX, ALP and OC) in MC3T3-E1 cells cultured for 2 days. Data were normalized to reference genes (GAPDH and 18S rRNA). Data represent fold changes of target genes normalized to reference genes (GAPDH and 18S rRNA), expressed as a percentage of the EtOH UV-untreated group, which was set to 100%. Values represent the mean±SEM (N=4). Student's t-test ($p<0.05$): $^a$7-DHC UV-treated vs the corresponding 7-DHC UV-untreated and $^b$treatment vs the corresponding EtOH control.

Figure 9:
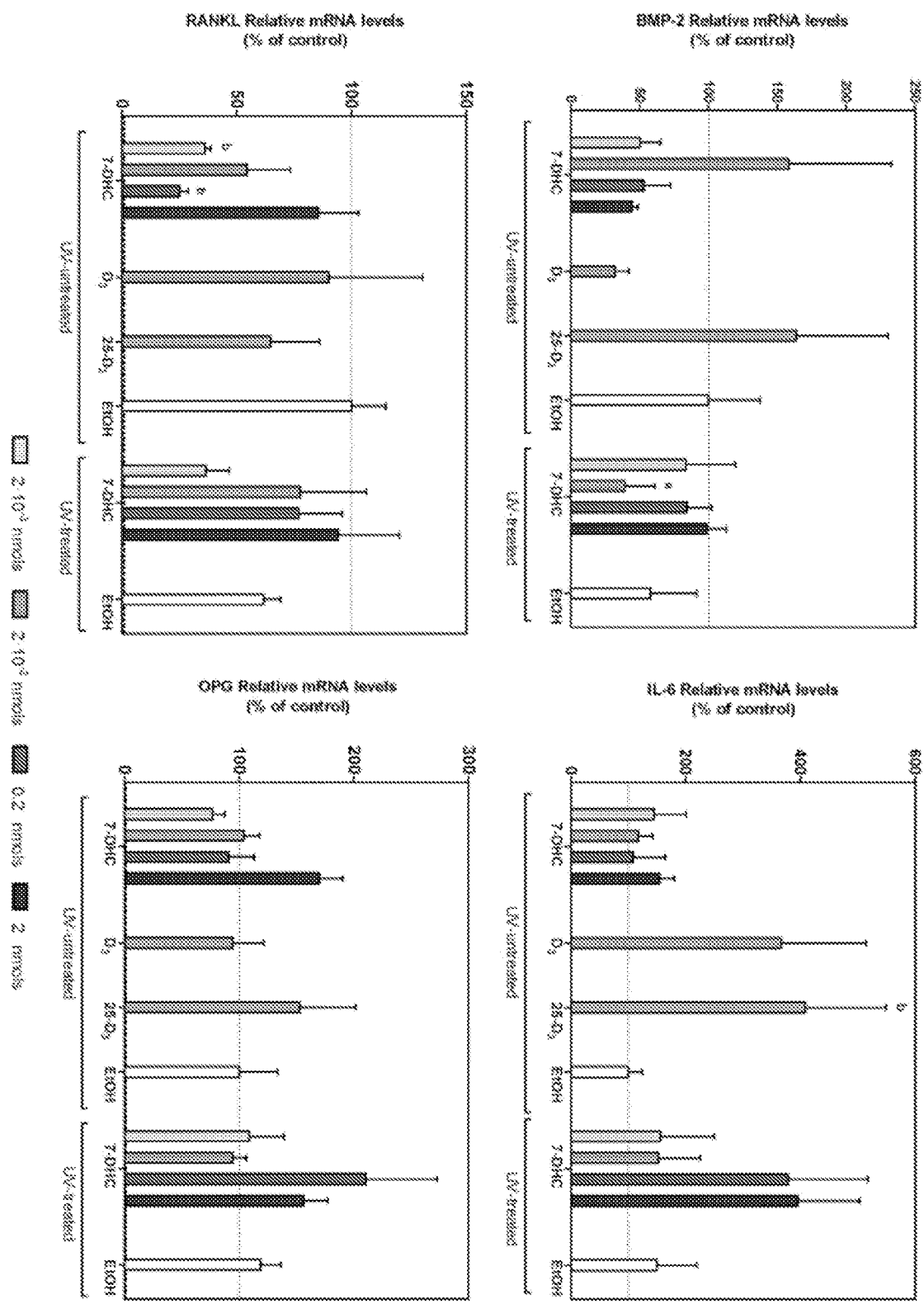

FIG. 9 shows the effect of the different treatments on gene expression levels of bone markers (BMP-2, IL-6, RANKL and OPG) in MC3T3-E1 cells cultured for 2 days. Data were normalized to reference genes (GAPDH and 18S rRNA). Values represent the mean±SEM (N=4). Student's t-test ($p<0.05$): $^a$7-DHC UV-treated vs the corresponding 7-DHC UV-untreated and $^b$treatment vs the corresponding EtOH control.

Figure 10:
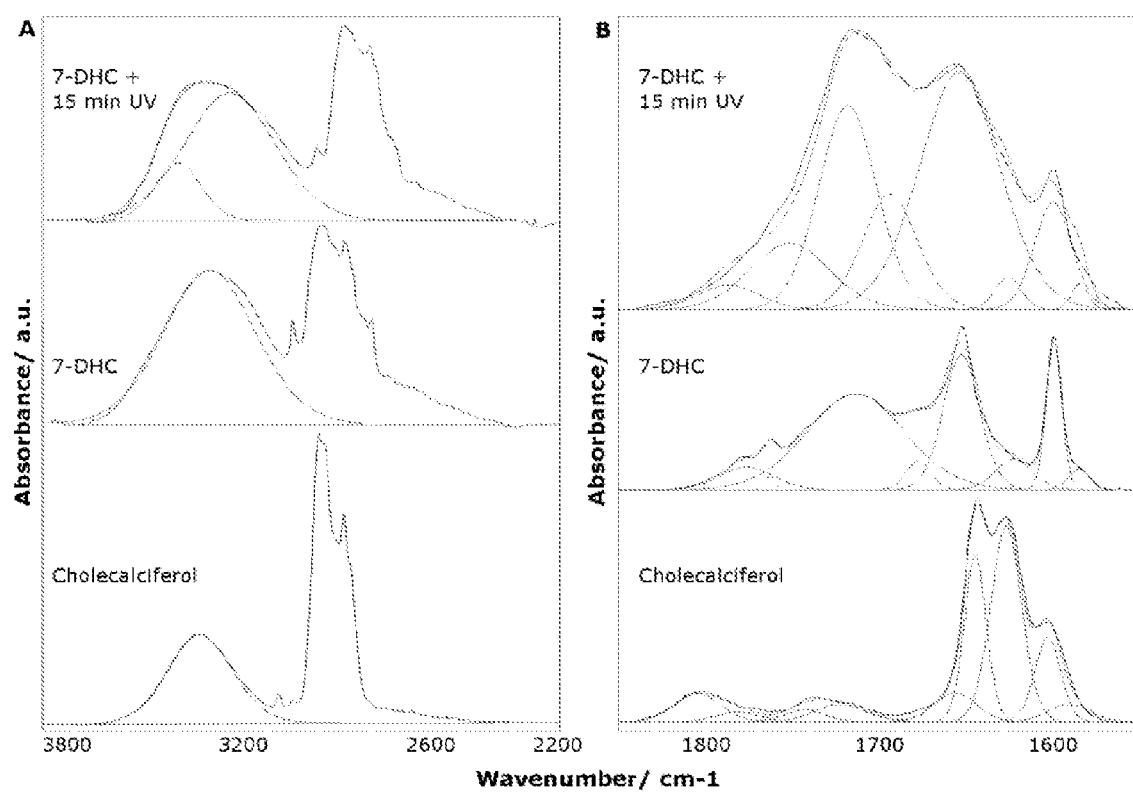

FIG. 10 provides a comparison of FTIR spectra for Cholecalciferol, non-irradiated 7-DHC, and 7-DHC irradiated for 15 min. The absorbances in the regions 3800 cm$^{-1}$ to 2200 cm⁻¹ (A) and 1850 cm⁻¹ to 1550 cm⁻¹ (B) are shown with the respective peaks fitted into the spectra.

Figure 11:
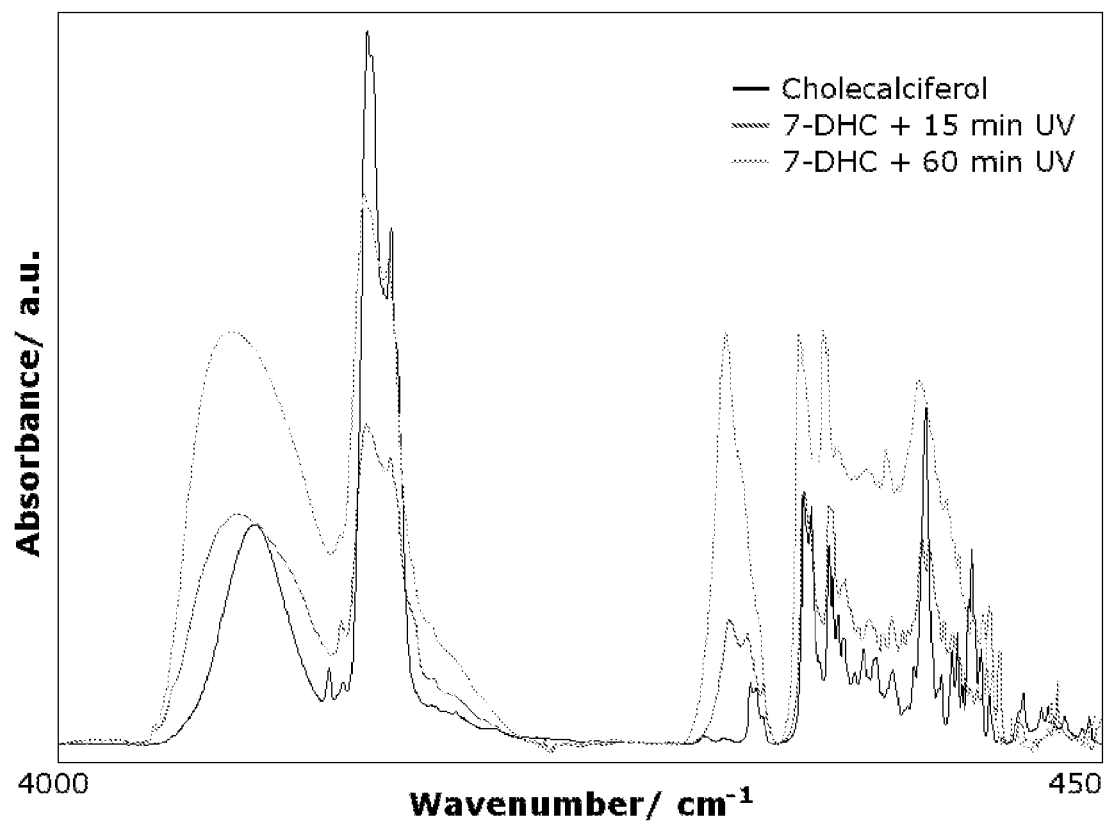

FIG. 11 provides a comparison of the absorbance spectra for cholecalciferol, 7-DHC after 15 min of UV irradiation, and 7-DHC after 60 min of UV irradiation for the entire wavenumber region measured (4000 cm⁻¹ to 450 cm⁻¹). The differences in the spectra were increasing with irradiation time.

Figure 12:
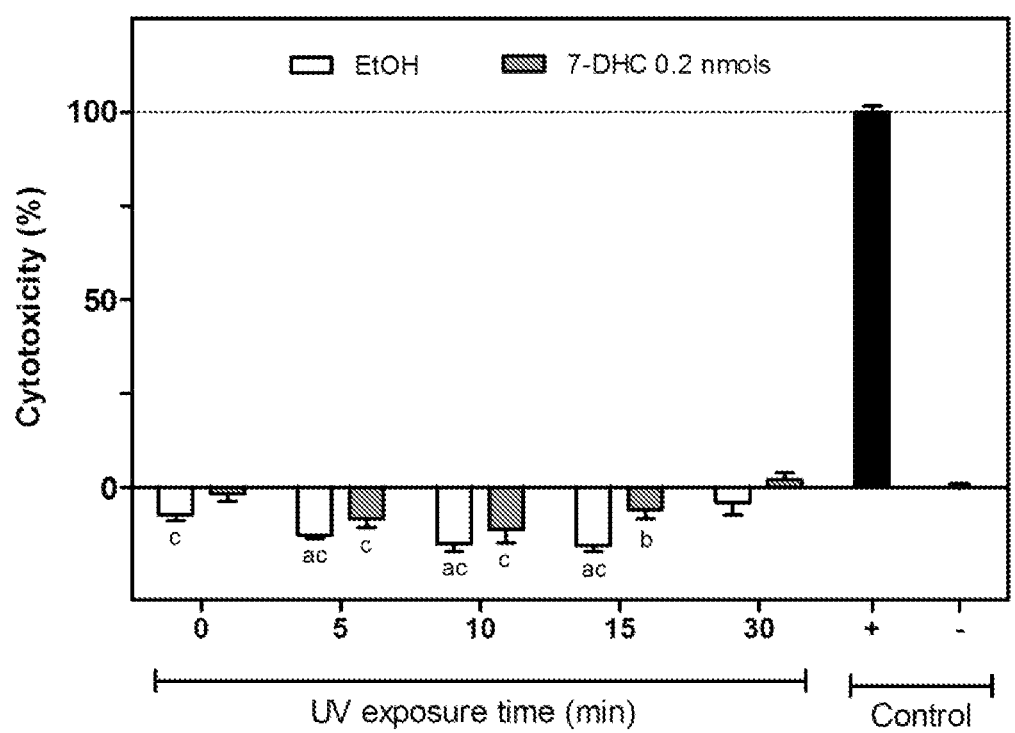

FIG. 12 shows the effect of UV time exposure of 7-DHC coated implants on cell viability after 24 hours of cell seeding. Positive control (+; 100% toxicity) was cell culture media from cells incubated with Triton X-100 at 1%. Negative control (−; 0 toxicity) was cell culture media from untreated cells cultured on plastic wells (TCP). Values represent the mean±SEM. Student's t-test ($p<0.05$): $^a$UV-treated vs UV-untreated for 7-DHC and ethanol, respectively; $^b$7-DHC treatment vs the corresponding ethanol control at each UV irradiation time and $^c$treatments on Ti surfaces vs the negative control (TCP).

Figure 13:
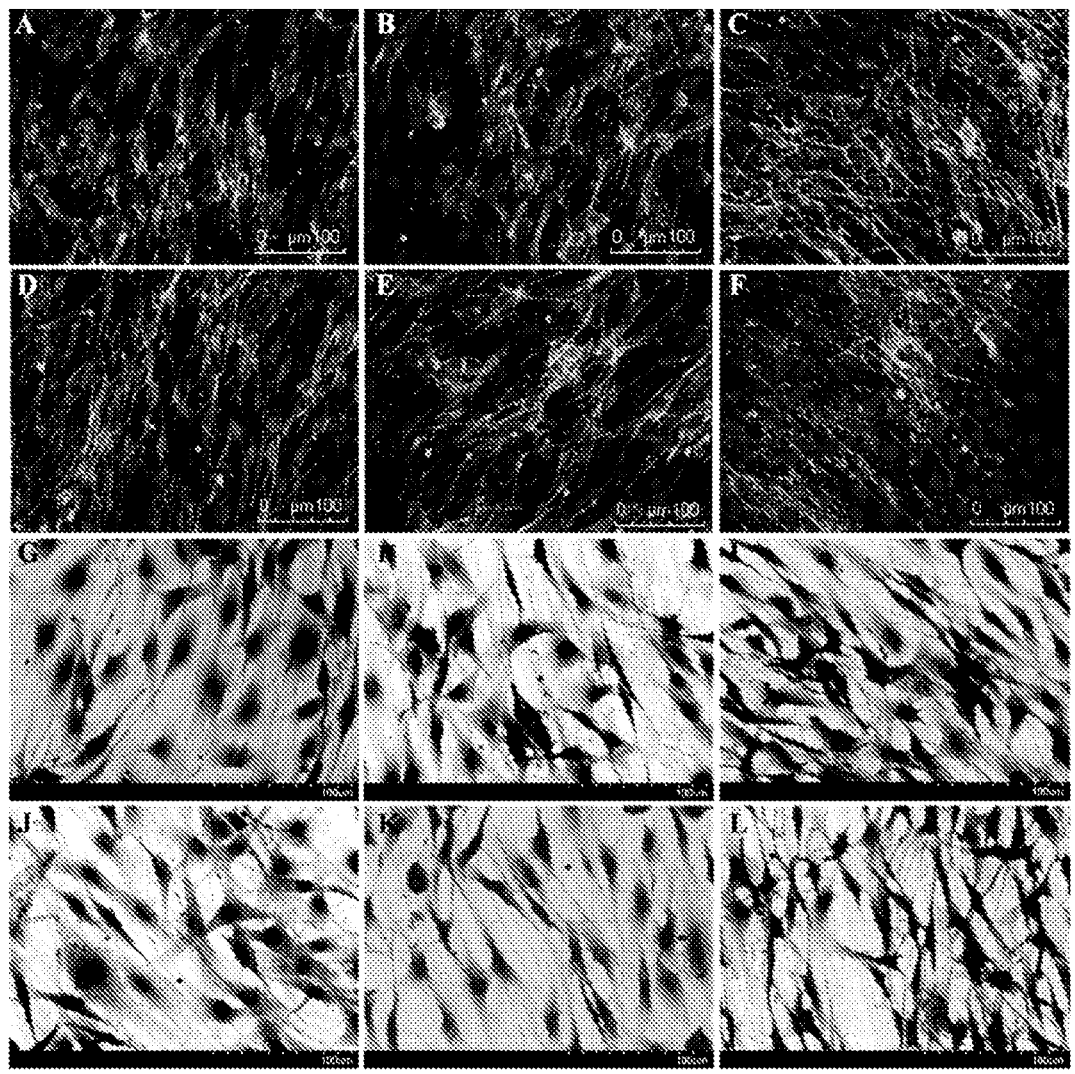

FIG. 13 shows the effect of UV time exposure of 7-DHC coated titanium implants on cell number and cell morphology. Representative images obtained from confocal laser scanning microscope of MC3T3-E1 cells cultured for 48 h are shown. Cells were stained with Phalloidin-FITC (stains actin filaments; green) and DAPI (stains nucleus, blue). 7-DHC treatment UV-exposed during 0 (A), 15 (b) and 30 minutes (C) and ethanol (control) coating also UV-treated for 0 (D), 15 (E) and 30 (F) minutes. In the same way, representative images from scanning electron microscope (SEM) after 48 hours of cell culture. Both 7-DHC (G-I) and ethanol (J-L) coating for different long UV time exposures, 0 (G and J), 15 (H and K) and 30 (I and L) minutes. (M) Values represent the mean±SEM (N=5) for total cell number per titanium implant and the percentage of titanium surface covered with MC3T3-E1 cells. Student's t-test ($p<0.05$) $^a$UV-treated vs UV-untreated for 7-DHC and ethanol, respectively.

Figure 14:
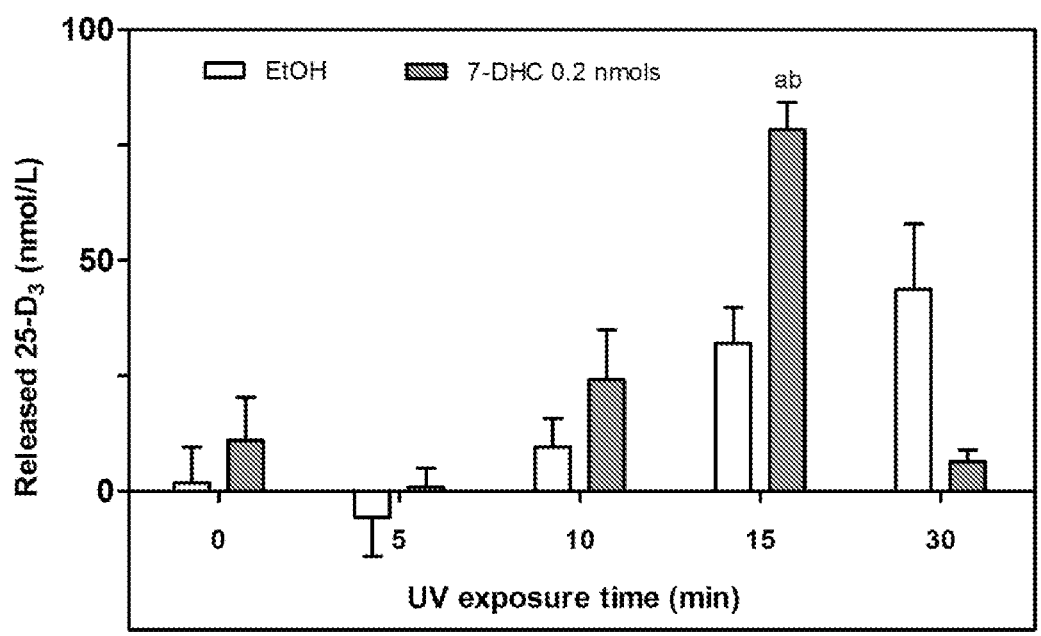

FIG. 14 shows the effect of UV time exposure of 7-DHC coated titanium implants on 25-D₃ secretion after 24 hours of cell seeding. Values represent the mean±SEM. Student's t-test ($p<0.05$): $^a$UV-treated vs UV-untreated for 7-DHC and ethanol, respectively; $^b$7-DHC treatment vs the corresponding ethanol control at each UV irradiation time.

Figure 15:
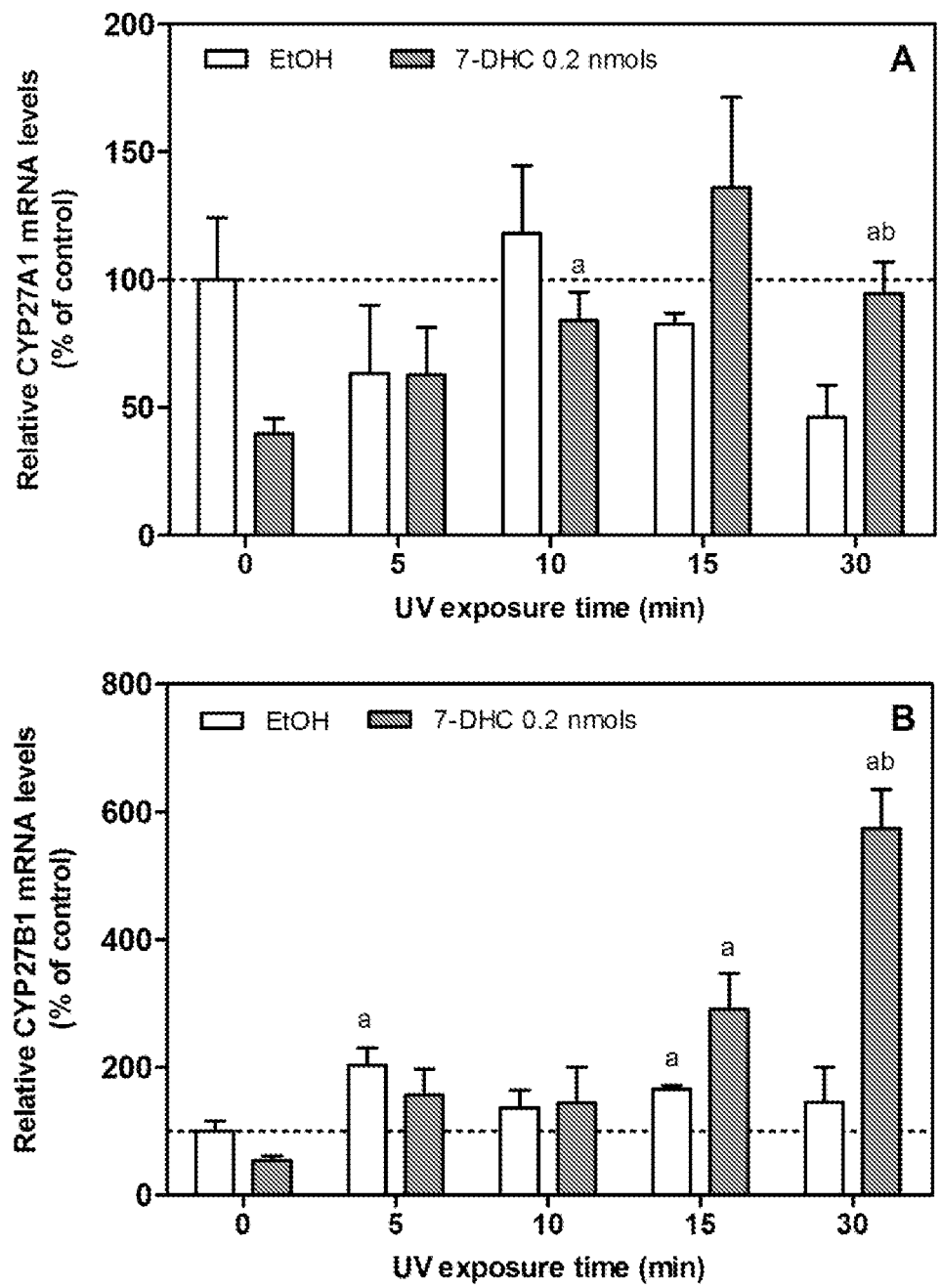

FIG. 15 shows the effect of UV time exposure of 7-DHC coated titanium implants on gene expression of hydroxylase enzymes after 48 h of cell seeding. Data represent fold changes of target genes normalized to reference genes (GAPDH, 18S rRNA), expressed as a percentage of the ethanol UV-untreated group, which was set to 100%. Values represent the mean±SEM (N=4). Student's t-test ($p<0.05$): $^a$UV-treated vs UV-untreated for 7-DHC and ethanol, respectively; $^b$7-DHC treatment vs the corresponding ethanol control at each UV irradiation time.

Figure 16:
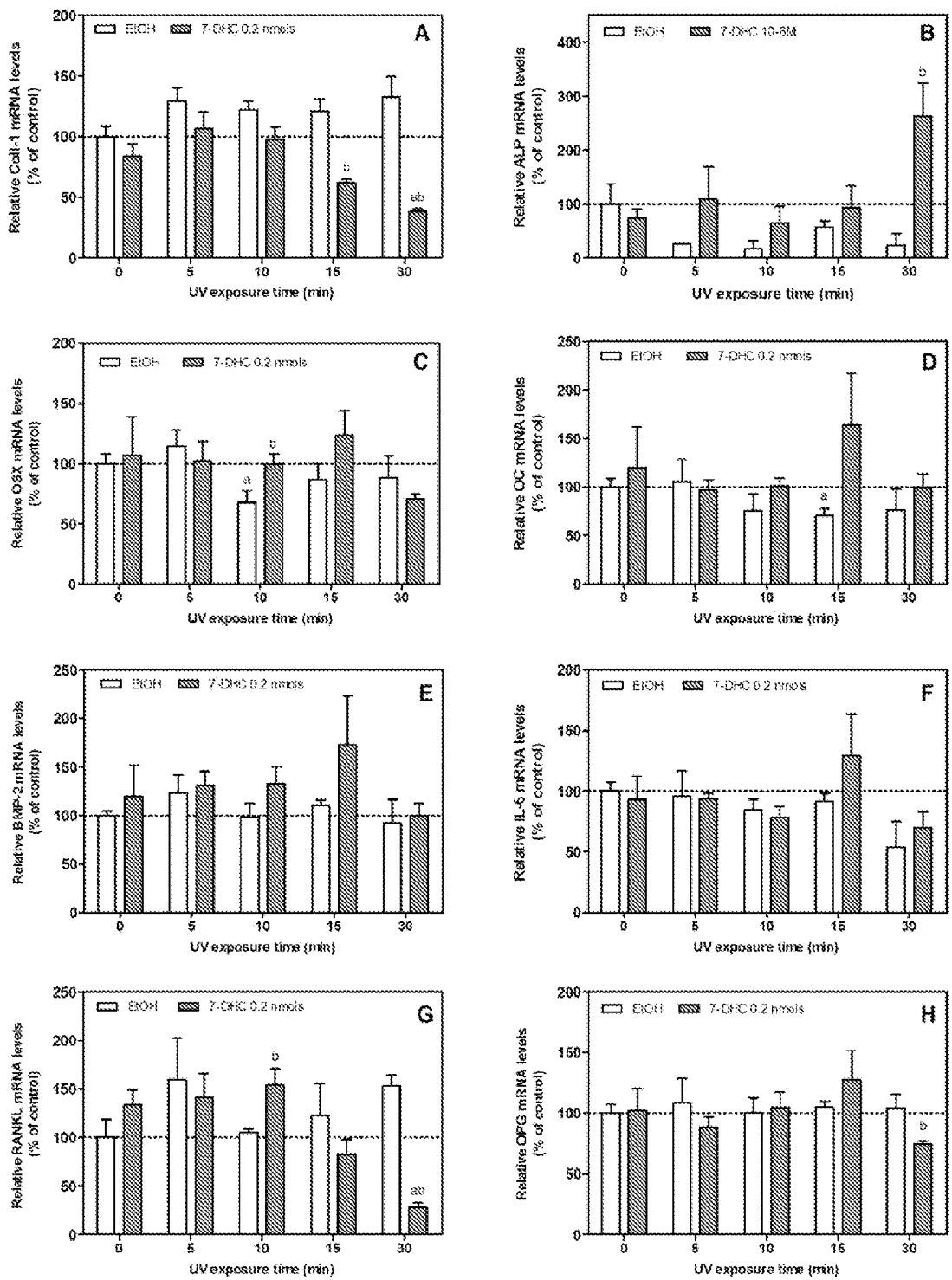

FIG. 16 shows the effect of UV time exposure of 7-DHC coated titanium implants on osteoblast differentiation. Several bone markers (Coll-1, OSX, ALP, OC, BMP-2, IL-6, RANKL and OPG) were analysed in MC3T3-E1 cells cultured for 48 h. Data were normalized to reference genes (GAPDH and 18S rRNA). Data represent fold changes of target genes normalized to reference genes (GAPDH and 18S rRNA), expressed as a percentage of the EtOH UV-untreated group, which was set to 100%. Values represent the mean±SEM. Student's t-test ($p<0.05$): $^a$UV-treated vs UV-untreated for 7-DHC and ethanol, respectively; $^b$7-DHC treatment vs the corresponding ethanol control at each UV irradiation time.

Figure 17:
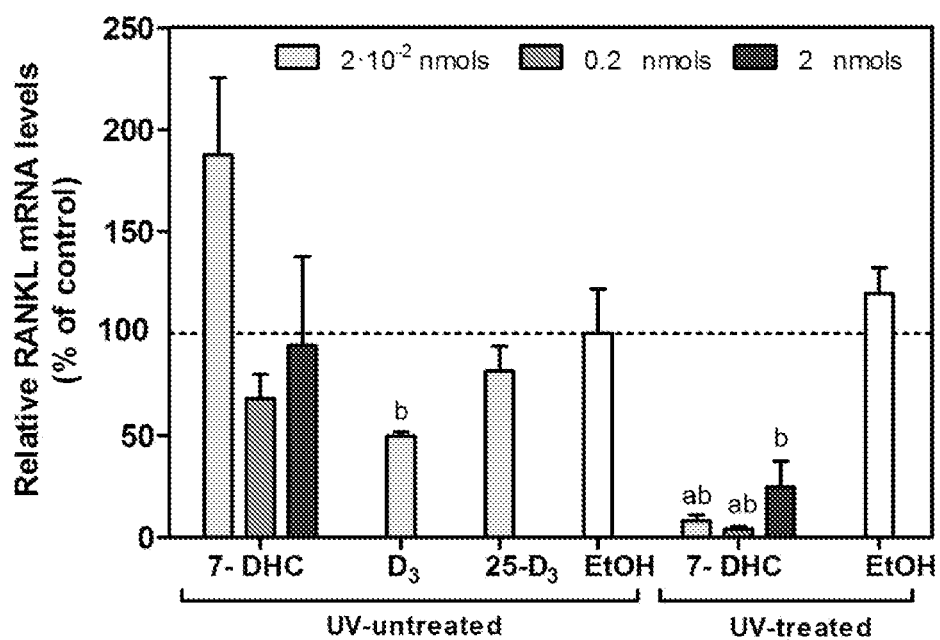

FIG. 17 shows the effect of the different treatments (7-DHC, D₃, 25-D₃) and UV exposure of titanium implants on RANKL gene expression in MC3T3-E1 cells cultured for 48 h. Data were normalized to reference genes (GAPDH and 18S rRNA). Values represent the mean±SEM. Student's t-test ($p<0.05$): $^a$UV-treated vs UV-untreated for 7-DHC and ethanol, respectively; $^b$7-DHC treatment vs the corresponding ethanol control.

Figure 18:
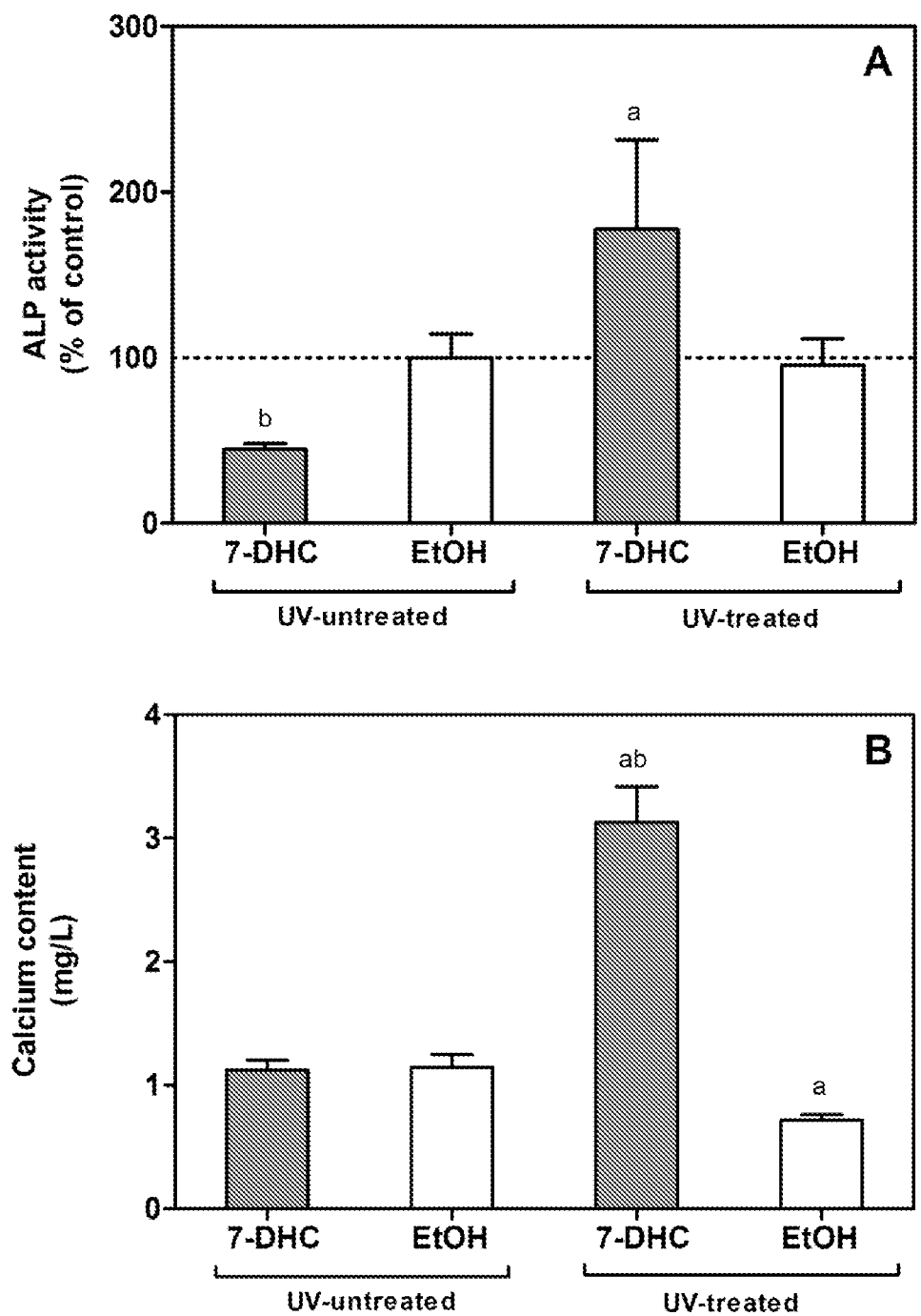

FIG. 18 shows the effect of the different treatments (7-DHC, D₃, 25-D₃) and UV exposure of titanium implants on alkaline phosphatase (ALP) activity and mineralization. (A) ALP activity measured at 21 days of MC3T3-E1 culture. Data were normalized to protein concentration and expressed as a percentage of the ethanol UV-untreated group, which was set to 100%. (B) Calcium content measured at 28 days of MC3T3-E1 culture. Values represent the mean±SEM. Student's t-test ($p<0.05$): $^a$UV-treated vs UV-untreated for 7-DHC and ethanol, respectively; $^b$7-DHC treatment vs the corresponding ethanol control.

Figure 19:
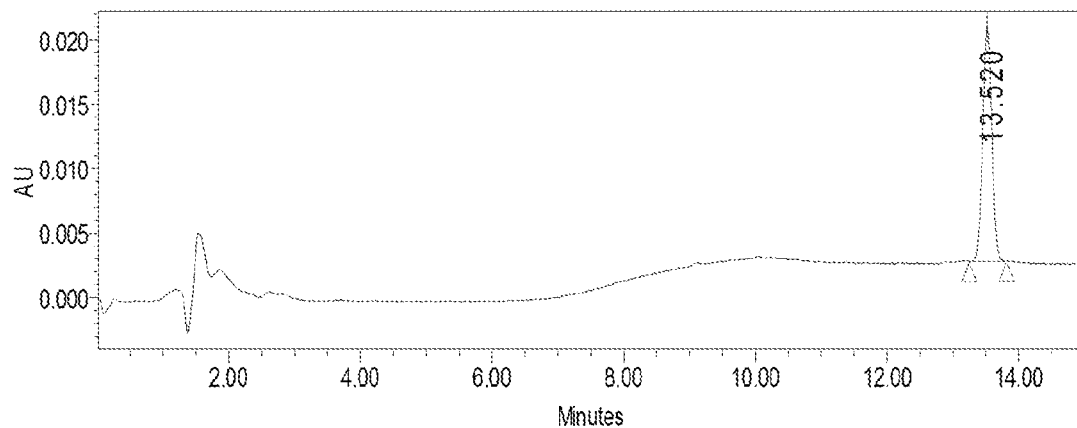

FIG. 19 shows the HPLC chromatogram of a 7-DHC+Vit E non-irradiated sample (titanium substrate). Only 7-DHC is detected, eluting at 13.5 min retention time.

Figure 20:
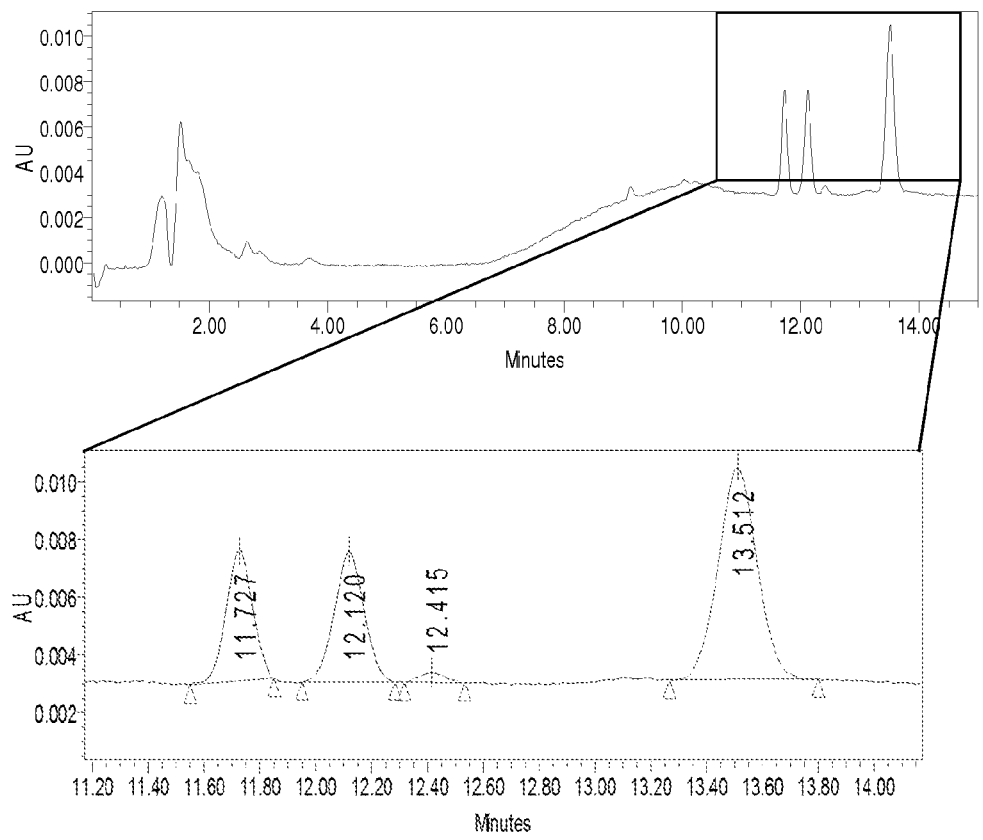

FIG. 20 shows the HPLC chromatogram of a 7-DHC irradiated sample. Vitamin D₃ elutes at 11.7 min, Lumisterol at 12.1 min and 7-DHC at 13.5 min. A small peak at 12.4 min is attributed to tachysterol.

Figure 21:
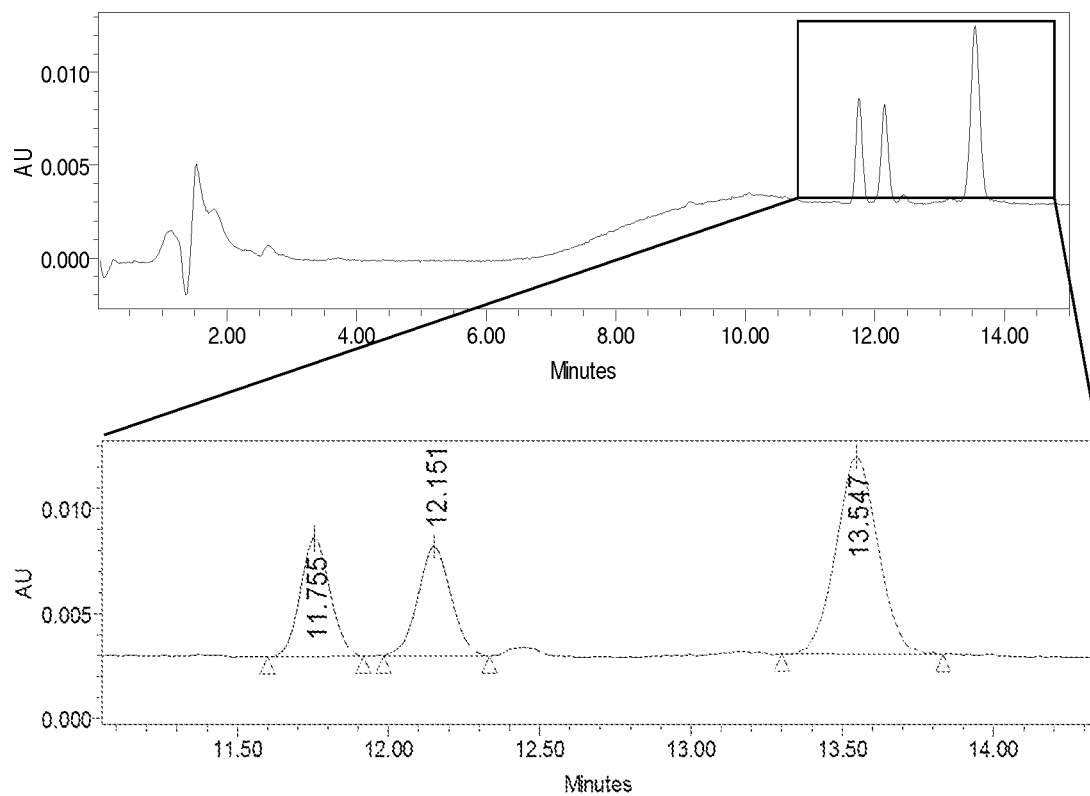

FIG. 21 shows the HPLC chromatogram of a 7-DHC+Vit E irradiated sample. Vitamin D₃ elutes at 11.7 min, Lumisterol at 12.1 min and 7-DHC at 13.5 min.retention time.

EXAMPLES

Example 1

Obtaining a UV Irradiated Titanium Implant Treated with 7-DHC

Titanium (Ti) surfaces were coated with either 7-DHC or cholecalciferol to analyse their transition initiated by UV light. The aim of the study was showing how specific the UV initiated conversion from 7-DHC to cholecalciferol was and which irradiation time would be the most appropriate.

1.1. Materials and Methods

7-DHC and cholecalciferol were purchased from Sigma-Aldrich with the highest grade of purity available. Surfaces of Ti (c.p. grade IV) disks, 6.25 mm in diameter, were coated with either 7-DHC or cholecalciferol. The surfaces were dried on air and subsequently irradiated with UV light ($\lambda=302$ nm, P=6 W, distance to surfaces 43 mm, lamp purchased from VWR, Oslo, Norway). The samples were analysed with FTIR spectroscopy (DRIFT) after 0 min, 15 min, 30 min, and 60 min of irradiation. An equally irradiated, uncoated Ti disk was used as a background for the FTIR measurements. The spectra obtained by FTIR spectroscopy were analysed for typical absorbances connected with photooxidation of the surface coatings. Typical peak areas were quantified if possible and will be subsequently compared and discussed.

1.2. Results

The most important absorbances that showed changes in the chemical structure of 7-DHC and cholecalciferol due to UV irradiation are given in the following table (Table 1):

TABLE 1

Important changes of absorbances in FTIR spectroscopy for 7-DHC and cholecalciferol

| Wavenumber (max absorbance) | Group | Changes caused by UV irradiation of 7-DHC and cholecalciferol |
|---|---|---|
| 3300 cm−1 | —OH | no changes |
| 1730 cm−1 | C═O ester groups | increase |
| 1710 cm−1 | C═O carboxylic acids | increase |
| 1680 cm−1 | C═C trans | appearance and increase |
| 1650 cm−1 | C═C cis | increase |
| 1625 cm−1 | C═C aromatic | increase |

Figure 1:
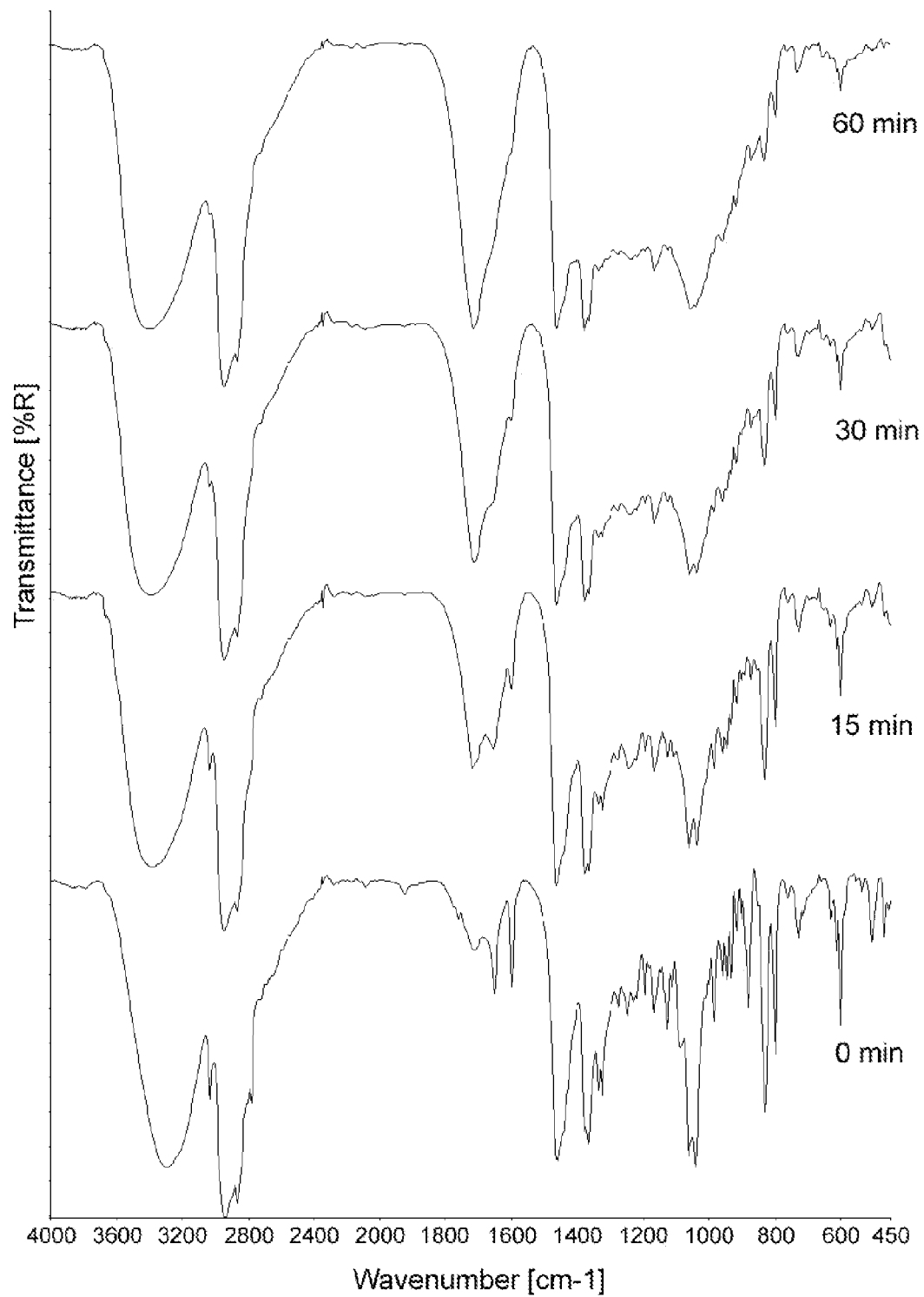
FIG. 1 shows FTIR spectra for 7-DHC that was irradiated with UV light for different periods of time.
Figure 2:
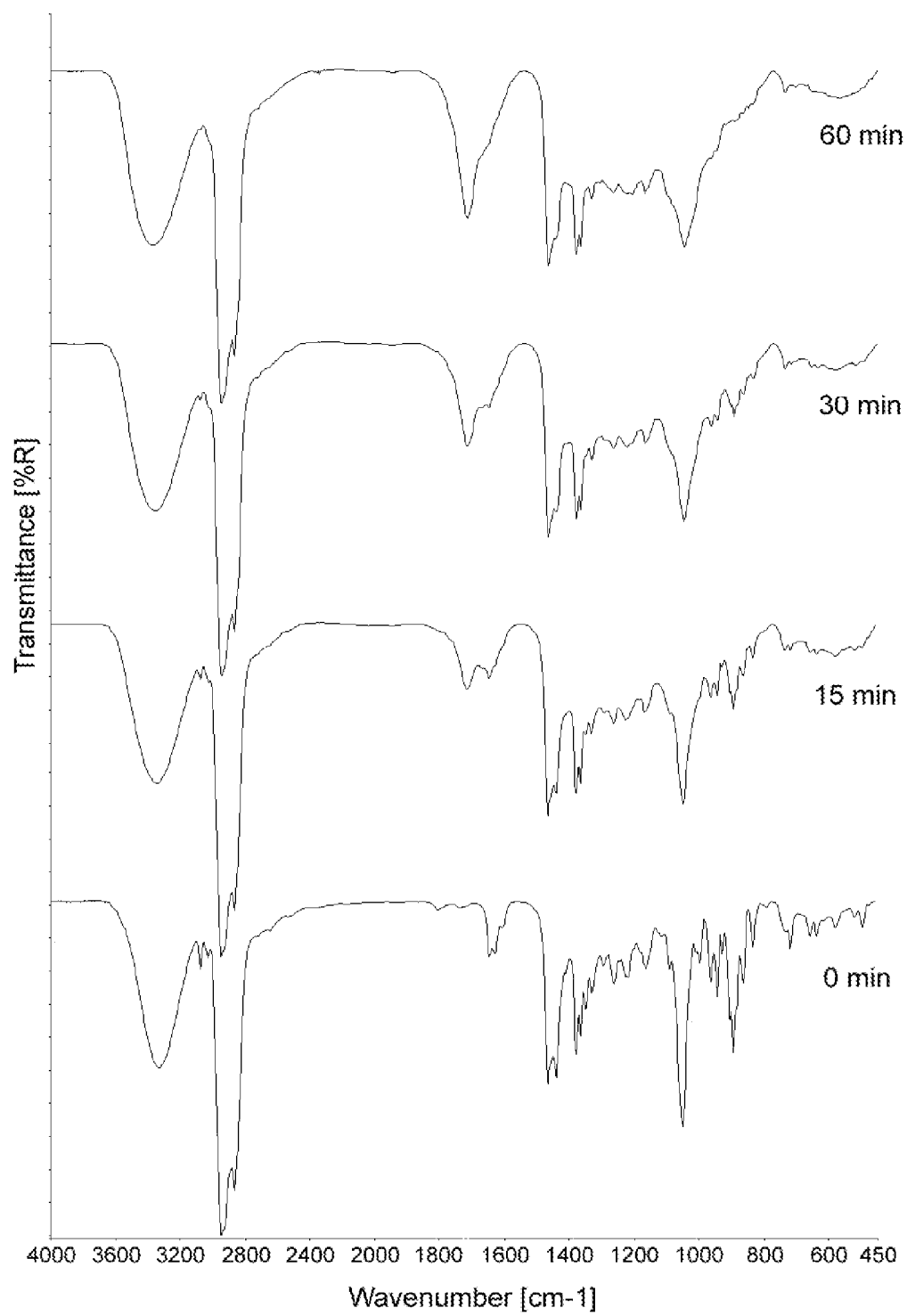
FIG. 2 shows FTIR spectra for cholecalciferol that was irradiated with UV light for different periods of time.

FIGS. 1 and 2 show how the absorbance spectra of 7-DHC and cholecalciferol were changing with UV irradiation time. As the chemical structures of the two substances are very alike, the absorbance spectra appeared to be quite similar. Also their behaviour with UV irradiation time appeared to be comparable (Table 1).

Figure 3:
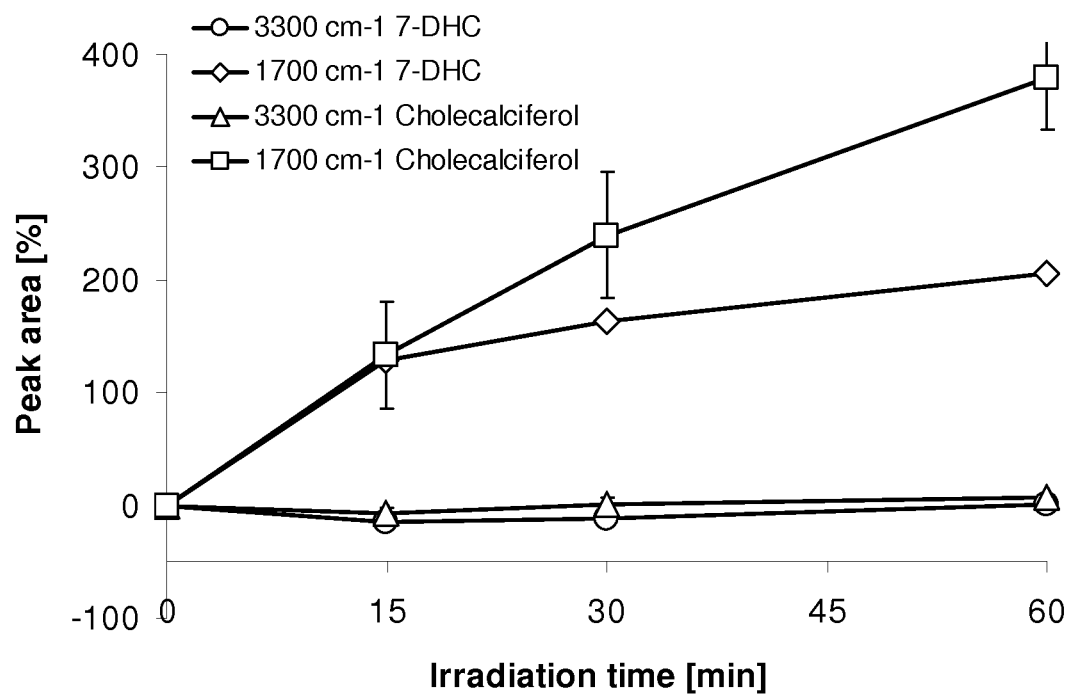
FIG. 3 shows changes of peak areas with UV irradiation time for the absorbance spectra of 7-DHC and cholecalciferol.

From the absorbance spectra and the changes of peak areas measured (FIG. 3), can be assumed that no —OH groups were generated due to the irradiation. The peak area at 3300 cm$^{-1}$ was stable with UV irradiation time. The peak area at about 1700 cm$^{-1}$ (including the area from 1850 cm$^{-1}$ to 1550 cm$^{-1}$) was increasing clearly for both substances, indicating the formation of C═C double bonds (aromatic, cis- and trans-), as well as the formation of C═O ester and carboxylic groups.

Example 2

Determination of Effects of UV Irradiation on the Conversion of 7-Dehydrocholesterol (7-DHC) into Biologically Active Vitamin D (1,25-$D_3$) and Changes in Gene Expression of the Key Enzymes Regulating its Hydroxylation, CYP27B1 and CYP27A1

2.1. Preparation of Irradiated Plastic Surfaces Covered with 7-DHC

For the treatment with vitamin D metabolites, stock solutions of 2 mM 7-Dehydrocholesterol (7-DHC, Sigma St. Louis, Mo., USA), 2 µM cholecalciferol ($D_3$, Sigma St. Louis, Mo., USA), and 2 µM 25-Hydroxyvitamin D (25-$D_3$, Sigma St. Louis, Mo., USA) were prepared in absolute ethanol and filtered with a 0.22 mm pore size filter before use. Fourteen different groups were prepared; eight were non irradiated: 7-DHC at different doses (20 nmols, 2 nmols, 0.2 nmols, $2 \times 10^{-2}$ nmols, and $2 \times 10^{-3}$ nmols), $2 \times 10^{-2}$ nmols $D_3$, $2 \times 10^{-2}$ nmols 25-$D_3$ and ethanol. And six were UV-irradiated: 7-DHC at the same different doses (20 nmols, 2 nmols, 0.2 nmols, $2 \times 10^{-2}$ nmols, and $2 \times 10^{-3}$ nmols) and ethanol.

To treat tissue culture plastic (TCP) wells, 10 µl of each dilution treatment were left on the surfaces and were allowed to air-dry for 15 min in the sterile flow bench. For UV-irradiation, a UV lamp of 302 nm was used at an intensity of irradiation of 6 mW/cm$^2$ (UVP, Upland, Calif., USA) during 30 minutes. Treated surfaces were immediately used for cell culture experiments.

2.2. Cell Culture

The mouse osteoblastic cell line MC3T3-E1 (DSMZ, Braunschweig, Germany) was selected as an in vitro model. Cells were routinely cultured at 37° C. in a humidified atmosphere of 5% $CO_2$, and maintained in α-MEM (PAA Laboratories GmbH, Pasching, Austria) supplemented with 10% fetal calf serum (FCS, PAA Laboratories GmbH, Pasching, Austria) and antibiotics (50 IU penicillin/ml and 50 µg streptomycin/ml, Sigma, St. Louis, Mo., USA). Cells were subcultured 1:4 before reaching confluence using PBS and trypsin/EDTA. All experiments were performed after eight passages of the MC3T3-E1 cells.

To test the effect of the different treatments onto the plastic wells, 96-well plates made of polystyrene were used and the treatments with 7-DHC performed directly onto them. Cells grown onto untreated TCP were added as a control for all the experiments. Cells were seeded at a density of 30,000 cells/cm$^2$ and they were maintained in α-MEM supplemented with 10% FCS and antibiotics. Culture media was collected after 48 hours, to test cytotoxicity and the production of the hydroxylated forms of vitamin D. Cells were harvested after 2 days of culture using Trizol reagent (Roche Diagnostics, Mannheim, Germany), to analyse early gene expression response of several osteoblast differentiation markers and enzymes involved in vitamin D synthesis using real-time RT-PCR.

MC3T3-E1 cells were also seeded on TCP without treatment and cultured up to 28 days to characterize the temporal gene expression profile of the enzymes involved in vitamin D synthesis. RT-PCR analyses were done after 1, 7, 14, 21, and 28 days of cell differentiation.

2.3. Determination of Cell Viability: LDH Activity

Lactate dehydrogenase (LDH) activity in the culture media was used as an index of cell death. LDH activity was determined spectrophotometrically after 30 min incubation at 25° C. of 50 µl of culture and 50 µl of the reaction mixture by measuring the oxidation of NADH at 490 nm in the presence of piruvate following the manufacturer's protocol (Cytotoxicity Detection Kit (LDH), Roche Diagnostics, Mannheim, Germany). Toxicities were presented relative to the LDH activity in the media of cells seeded on TCP without treatment (low control, 0% of cell death) and on cells grown on TCP treated with 1% Triton X-100 (high control, 100% of death), using the following equation:

Cytotoxicity (%)=(exp.value−low control)/(high control−low control)*100

Results related to cytotoxicity measured as LDH activity are shown in FIG. 4.

2.4. Quantitative Determination of 25(OH)D and 1,25(OH)$_2$D Released to the Culture Media 25-$D_3$ and 1,25-$D_3$ released to the culture media after two days of treatment were analyzed by enzyme-linked immunosorbent assay (ELISA). Aliquots from the culture media were centrifuged at 1800 rpm for 5 minutes at 4° C. and supernatants were used for 25-$D_3$ and 1,25-$D_3$ determination following instructions described by the manufacturer (Immunodiagnostic Systems Ltd, Boldon, Tyne and Wear, UK).

2.5. RNA Isolation

RNA was isolated from cells using a monophasic solution of phenol and guanidine thiocyanate (Trizol, Roche Diagnostics, Mannheim, Germany) according to the manufacturer's protocol. RNA was quantified at 260 nm using a Nanodrop spectrophotometer (NanoDrop Technologies, Wilmington, Del., USA).

2.6. Real-Time RT-PCR Analysis

Total RNA previously isolated was reverse-transcribed to cDNA using High Capacity RNA to cDNA kit (Applied Biosystems, Foster City, Calif.) according to the protocol of the supplier. The same amount of total RNA from each sample was converted into cDNA. Each cDNA was diluted ¼ and aliquots were stored at −20° C. until the PCR reactions were carried out.

Real-time RT-PCR was performed for two reference genes: 18S ribosomal RNA (18S rRNA), glyceraldehyde-3-phosphate dehydrogenase (GAPDH), and 11 target genes alkaline phospathase (ALP), Interleukin 6 (IL-6), Collagen (Coll-1), Osteocalcin (OC), Bone Morphogenetic Protein 2 (BMP-2), Osterix (Osx), Receptor activator of nuclear factor kappa-B ligand (RANKL), Osteoprogesterin (OPG) and genes involved in vitamin D synthesis such as Vitamin $D_3$ 25-hydroxylase (CYP27A1), 25 hydroxyvitamin $D_3$-1-alpha hydroxylase (CYP27B1) and 1,25-dihydroxyvitamin $D_3$ 24-hydroxylase (CYP24A1).

Real-time PCR were performed in the Lightcycler 480® (Roche Diagnostics, Germany). Each reaction contained 5 μl of LightCycler-FastStart DNA Master$^{PLUS}$ SYBR Green I (Roche Diagnostics, Mannheim, Germany), 0.5 μM of the sense and antisense specific primers (Table 1) and 3 μl of the cDNA dilution in a final volume of 10 μl. The normal amplification program consisted of a preincubation step for denaturation of the template cDNA (10 min 95° C.), followed by 45 cycles consisting of a denaturation step (10 s 95° C.), an annealing step (10 s 60° C., except for ALP that was 10 s at 65° C., OSX with 10 s at 68° C. and CYP24A1 at 58° C. 10 s) and an extension step (10 s 72° C.). After each cycle, fluorescence was measured at 72° C. Every run included a negative control without cDNA template. To confirm amplification specificity, PCR products were subjected to a melting curve analysis on the LightCycler and subsequently 2% agarose/TAE gel electrophoresis, Tm and amplicon size, respectively.

To allow relative quantification after PCR, real-time efficiencies were calculated from the given slopes in the Light-Cycler 480 software (Roche Diagnostics, Mannheim, Germany) using serial dilutions. Relative quantification after PCR was calculated by normalizing target gene concentration in each sample by the concentration mean of the two reference genes in given sample using the "advanced relative quantification method" provided by the LightCycler 480 analysis software.

2.7. Statistics

All data are presented as mean values ±standard error of the mean (SEM). Dose-response curves for 7-DHC were fitted with nonlinear regression analysis for sigmoid curves, using GraphPad Prism version 5.00 for Windows (GraphPad Software, San Diego Calif., USA). Differences between groups were assessed by Mann-Whitney-test or by Student t-test depending on their normal distribution. The SPSS® program for Windows, version 17.0 was used. Results were considered statistically significant at the p-values ≤0.05.

2.8. Results a) Effect of Treatments on Osteoblast Viability

LDH activity was measured in the culture media after 24 hours of culture as an index of toxicity (FIG. 4). All the non-UV-treated groups showed improved cell viability compared to the low control (cells seeded on TCP without any treatment). Although significant differences were found when comparing the UV-treated 7-DHC groups versus their corresponding non-UV-treated 7-DHC groups or compared to the ethanol UV-treated group, only the higher dose of 7-DHC when UV exposed displayed a toxic effect (as compared to the low control).

b) Temporal Gene Expression of CYP27A1, CYP27B1 and CYP24A1 in Osteoblastic Cells In order to investigate the capability of osteoblasts to endogenously synthesize the active form of vitamin D, we first characterized temporal mRNA expression levels of different genes involved in vitamin D hydroxylation (CYP27A1 and CYP27B1) and the gene involved in its degradation (CYP24A1) at different time-points (1, 7, 14, 21 and 28 days) by real-time RT-PCR (FIG. 5) osteoblast differentiation. As regards to the enzyme responsible of 1,25-dihydroxyvitamin $D_3$ degradation, CYP24A1, no constitutive gene expression could be detected MC3T3-E1 cells at the different time points analyzed.

c) Effect of Treatments on Gene Expression of Enzymes Involved in Vitamin D Synthesis Once the constitutive expression of CYP27A1 and of CYP27B1 in MC3T3-E1 cells was confirmed, the effect of treatments on its expression levels was analyzed. A trend to high expression levels of CYP27A1 was found for the lower dose of 7-DHC treatment in both cases, when UV-treated and UV-untreated, although statistical significance was not reached (see FIG. 6). For the rest of 7-DHC UV-treated doses analyzed a dose-response increase on CYP27A1 mRNA levels was found, showing significant differences compared to the UV-untreated corresponding doses. It should be also noted that the EtOH UV-treated group also showed an increase in CYP27A1 mRNA levels. As regards to CYP27B1, an increase in mRNA levels was found for the higher concentrated 7-DHC samples which have been UV-irradiated, although significance was not reached.

CYP24A1 was not constitutively expressed, but it was investigated if its expression could be induced by any of the treatments. In fact, it was found that CYP24A1 mRNA levels were only detected in cells treated with 25-$D_3$ (data not shown).

d) Effect of Treatment on the Release of 25-$D_3$ and 1,25$D_3$ into the Cell Culture Media To confirm the production of 25-$D_3$ and 1,25-$D_3$ by MC3T3-E1 cells, these metabolites were quantified in cell culture media by ELISA after 48 hours of treatment (FIG. 7). In agreement with the hypothesis, when 7-DHC was activated by UV irradiation a dose-response was found for both, the production of 25-$D_3$ and of the final active vitamin D (1,25-$D_3$), while no dose-response was detected when 7-DHC was not UV-treated. Therefore, UV-irradiation is required to yield active vitamin D production from 7-DHC. The $D_3$ and 25-$D_3$ groups were added to the experiment as controls. As expected, high concentrations of 25-$D_3$ were found for the 25-$D_3$ treated group, 415±20 nmol/L were released to culture media and only 42±4 pmol/L of 1,25-$D_3$ were detected in culture media. Cells treated with $2\times10^{-2}$ nmols of $D_3$ showed 9.1±1.9 nmol/L and 19.7±0.7 pmol/L of 25-$D_3$ and of 1,25-$D_3$ respectively.

e) Effect of Treatment on Gene Expression of Several Osteoblast Markers

Several reports have demonstrated that vitamin D regulates osteoblast differentiation and mineralization, but the effect of 7-DHC UV-irradiated and non-UV-irradiated was unknown. For this reason, real-time RT-PCR was performed to observe the effect of the different vitamin D precursor treatments on bone markers (FIGS. 8 and 9). Collagen type-1 showed increased mRNA levels in cells treated with 0.2 nmols 7-DHC UV-treated compared to the same treatment non UV-irradiated. Higher expression levels of Osterix were seen in all 7-DHC UV-treated groups compared to the non irradiated ones, showing statistical significance the 0.2 and 2 nmols groups. Higher ALP mRNA levels were found in cells treated with $2\times10^{-3}$ nmols 7-DHC UV-treated compared to the same treatment non UV-irradiated. As regards to Osteocalcin mRNA levels, statistical differences were just reached for the 2 nmols 7-DHC UV-treated group compared to the same treatment non UV-irradiated.

Bone morphogenetic protein 2 (FIG. 9) showed no important changes for the different groups of treatments. However, significantly lower levels were found for the $2\times10^{-2}$ nmols 7-DHC UV-treated group compared to the non-irradiated one. No significant differences were found when comparing IL-6 mRNA levels between the different 7-DHC doses when UV-treated and UV-untreated, although the highest doses of UV-treated DHC samples showed a trend to higher IL-6 mRNA levels. Treatment with $2\times10^{-2}$ nmols 25-$D_3$ induced significantly higher expression levels of this interleukin compared to control. RANKL mRNA levels were lower in some of the 7-DHC UV-untreated samples compared to their control. OPG mRNA levels showed no significant differences among the tested groups.

2.9. Conclusion

In relation of the cytotoxicity of UV-treatment, it is shown that although cells treated with UV-treated 7-DHC showed a decrease on cell viability compared to non UV-treated, only the highest 7-DHC dose used that was UV-irradiated was toxic to the cells. In fact, and in agreement with the LDH activity results, low levels of total RNA were obtained for this group and proper normalization of the data could not be achieved by the use of reference genes. Therefore the 20 nmols dose was excluded for gene expression analysis.

The exposed results revealed the highest 1,25-$D_3$ production for 25-$D_3$ treatment, but this performance does not appear in CYP27B1 mRNA levels for this treatment, suggesting that the product may induce a negative feedback. However, CYP27B1 mRNA expression in 25-$D_3$ treated samples was not statistically different. This result may be due to the early point (48 h) when the samples were analysed. As regards to CYP24A1, mRNA levels were detected only in 25-$D_3$ treated samples, which showed the higher 1,25-$D_3$ production. This finding is in accordance with previous studies revealing that 1,25-$D_3$ treatment upregulates CYP24A1 levels through a feedback system.

Once established the effect of the different treatments on mRNA expression levels of the enzymes responsible for vitamin $D_3$ hydroxylation, the levels of 25-$D_3$ and 1,25-$D_3$ released to cell culture media after 48 hours of treatment were analyzed. The data reveals a dose-dependent increase in both, the production of 25-$D_3$ and of 1,25-$D_3$ levels for UV-activated 7-DHC samples unlike UV-untreated ones, confirming the hypothesis that 7-DHC UV-treated is converted to active vitamin D directly by osteoblasts.

Active vitamin D acts directly on osteoblasts and regulates osteoblast differentiation. Therefore, the effect of the different treatments on the expression of different osteoblast related genes was analyzed. Collagen type-1, an early marker which supports the cell proliferation stage, osterix, a transcriptional factor involved in osteoblast differentiation, and osteocalcin, the most abundant non-collagenous protein in bone. These genes showed increased mRNA levels in cells treated with some of the higher doses of 7-DHC when UV-irradiated, pointing to an enhanced osteoblast differentiation in accordance with the effects observed by active vitamin D treatment.

In conclusion, the exposed data support for the first time the concept that the vitamin D precursor 7-DHC can be used, when combined with UV-irradiation, to locally produce active vitamin D and enhance osteoblast differentiation. The results found on osteoblast gene expression confirmed that treatment of MC3T3-E1 with UV-activated 7-DHC exerts a similar effect than 1,25-$D_3$ treatment of osteoblasts. It has been also demonstrated that the required enzymatic machinery for this pathway is present and biologically active in bone cells.

Example 3

Measurement of Osteoblast Differentiation end Expression of RANKL Gene on Titanium Implants Coated with 7-DHC and Fotoactivated with UV Light 3.1. Implants and Treatments Ti disks made of grade 2 and with a diameter of 6.25 mm and a height of 2 mm were machined from cp Ti rods and subsequently ground, polished, and cleaned. For the surface modification of Ti implants stock solutions of 2 mM 7-dehydrocholesterol (7-DHC, Sigma St. Louis, Mo., USA), 2 µM cholecalciferol ($D_3$, Sigma St. Louis, Mo., USA), and 2 µM 25-hydroxyvitamin D (25-$D_3$, Sigma St. Louis, Mo., USA) were prepared in absolute ethanol and filtered with a 0.22 µm pore size filter before use.

To treat implant surfaces, 10 µl of each dilution treatment were left on the surfaces and were allowed to air-dry for 15 min in the sterile flow bench. For UV-irradiation, a UV lamp of 302 nm was used at an intensity of irradiation ca. 6 mW/cm$^2$ during several irradiation times.

Different groups were prepared; (1) non-irradiated samples: 7-DHC ($2\times10^{-2}$, 0.2 and 2 nmols), $D_3$ and 25-$D_3$ ($2\times10^{-2}$ nmols) and ethanol (used as control for the non-irradiated groups, EtOH); and (2) UV-irradiated samples: 7-DHC ($2\times10^{-2}$, 0.2 and 2 nmols) and EtOH (used as control for the 7-DHC-irradiated group).

3.2. Fourier Transform Infrared Spectroscopy (FTIR) Analysis of 7-DHC and $D_3$ Coating on Ti Surfaces FTIR spectroscopy (DRIFT) (Spectrum 100, Perkin Elmer, USA) was used to analyze the effect of UV irradiation on vitamin D conversion after 0 min, 15 min, 30 min, and 60 min of UV irradiation. Titanium implants coated with 7-DHC or $D_3$ were UV-irradiated as previously described. An equally irradiated and untreated Ti implant was used as a background for the FTIR measurements. The spectra obtained by FTIR spectroscopy were analysed for typical absorbances connected with changes in chemical structure of 7-DHC and $D_3$ after UV exposure of the surface coatings (FIG. 10). The spectra were smoothened and baseline corrected with the program Spectrum (version 6.3.2.0151, PerkinElmer, Inc., Waltham, USA). Typical peak areas were fitted and the fitted curve areas were quantified with CasaXPS (version 2.3.15, Casa Software Ltd.) for comparison.

3.3. Cell Culture

The mouse osteoblastic cell line MC3T3-E1 (DSMZ, Braunschweig, Germany) was chosen as an in vitro model. Cells were regularly cultured at 37° C. in a humidified atmosphere of 5% $CO_2$, and maintained in α-MEM (PAA Laboratories GmbH, Pasching, Austria) supplemented with 10% fetal calf serum (FCS, PAA Laboratories GmbH, Pasching, Austria) and antibiotics (50 IU penicillin/ml and 50 µg streptomycin/ml, Sigma, St. Louis, Mo., USA). Cells were subcultured 1:4 before reaching confluence using PBS and trypsin/EDTA. All experiments were carried out after 8 passages of the MC3T3-E1 cells.

To test the effect of the surface modification, 96-well plates were used. Ti disks were placed into the wells and treatments and UV-activation were performed over there. Cells grown onto untreated polystyrene tissue culture plastic (TCP) were added as a control for all the experiments. Cells were seeded at a density of 30,000 cells/cm$^2$ and they were maintained in α-MEM supplemented with 10% FCS and antibiotics. Culture media was collected after 48 hours, to test cytotoxicity and the production of the hydroxylated form of vitamin D, 25-$D_3$. Cells were harvested after two days of culture using Trizol reagent (Roche Diagnostics, Mannheim, Germany), to analyze gene expression of several osteoblast differentiation markers and enzymes involved in vitamin D synthesis using real-time RT-PCR. On the other hand, MC3T3-E1 cells were harvested after 21 days to measure calcium content and ALP activity in the cell monolayer.

3.4. Determination of Cell Viability: LDH Activity

Lactate dehydrogenase (LDH) activity in the culture media was used as an index of cell death. LDH activity was determined spectrophotometrically after 30 min incubation at 25° C. of 50 μl of culture and 50 μl of the reaction mixture by measuring the oxidation of NADH at 490 nm in the presence of piruvate following the manufacturer's protocol (Cytotoxicity Detection Kit (LDH), Roche Diagnostics, Mannheim, Germany). Toxicities were presented relative to the LDH activity in the media of cells seeded on TCP without treatment (low control, 0% of cell death) and on cells grown on TCP treated with 1% Triton X-100 (high control, 100% of death), using the following equation: Cytotoxicity (%)=(exp.value−low control)/(high control−low control)×100.

3.5. Determination of Number of Cells

Cells growing on the different surfaces were lysed after 48 hours of cell culture by a freeze-thaw method in deionized distilled water. Cell lysates were used for determination of DNA quantity using Hoechst 33258 fluorescence assay. Samples were mixed with 20 μg/ml of Hoechst 33258 fluorescence stain (Sigma, St. Quentin Fallavier, France) in THE buffer at pH 7.4 containing 10 mM Tris-HCl, 1 mM EDTA and 2 M NaCl. The intensity of fluorescence was measured at excitation and emission wavelengths of 356/465 nm using a multifunction microplate reader (Cary Eclipse fluorescence spectrophotometer, Agilent Technologies, Santa Clara, United States). Relative fluorescence units were correlated with the cell number using a linear standard curve.

3.6. Cell Staining and Cell Morphology Analysis

Confocal images were obtained of cells growing in the different treated surfaces at 48 hours of cell culture. Cells were first fixed and then permeabilized and stained with Phalloidin-FITC (50 μg/ml) to stain actin filaments. Finally, a drop of DAPI was added to stain cell nucleus. Various images of each implant were taken with the confocal microscope (Leica DMI 4000B equipped with Leica TCS SPE laser system) by measuring fluorescence signal between 430-480 nm for DAPI and 500-525 nm for Phalloiding-FITC.

Images of cells were also captured with scanning electron microscope (SEM, Hitachi S-3400N, Hitachi High-Technologies Europe GmbH, Krefeld, Germany) at 48 hours of cell culture. Back Scattered Electrons (BSE), 40 Pa of pressure and 10 kV of voltage were applied. In this case, cells were washed twice with PBS and fixed with glutaraldehyde 4% in PBS for 2 hours. Then, the fixative solution was removed and the cells were washed with distilled water twice. At 30 minute intervals, the cells were dehydrated by the addition of 50%, 70%, 90% and 100% ethanol solutions. Ethanol was removed and the cells were left at room temperature to evaporate the remaining ethanol.

Quantitation of the percentage of titanium surface covered with MC3T3-E1 cells was achieved by analyzing the previous images with ImageJ software (Rasband, W. S., ImageJ, U. S. National Institutes of Health, Bethesda, Md., USA).

3.7. Quantitative Determination of 25-$D_3$ Released to the Culture Media

25-$D_3$ released to the culture media after 2 days of treatment were analyzed by enzyme-linked immunosorbent assay (ELISA). Aliquots from the culture media were centrifuged at 1800 rpm for 5 minutes at 4° C. and supernatants were used for 25-$D_3$ and determination following instructions described by the manufacturer (Immunodiagnostic Systems Ltd, Boldon, Tyne and Wear, UK).

3.8. RNA Isolation

RNA was isolated from cells using a monophasic solution of phenol and guanidine thiocyanate (Trizol, Roche Diagnostics, Mannheim, Germany) according to the manufacturer's protocol. RNA was quantified at 260 nm using a Nanodrop spectrophotometer (NanoDrop Technologies, Wilmington, Del., USA).

3.9. Real-Time Quantitative PCR Analysis

Total RNA previously isolated was reverse-transcribed to cDNA using High Capacity RNA to cDNA kit (Applied Biosystems, Foster City, Calif.) according to the protocol of the supplier. The same amount of total RNA from each sample was converted into cDNA. Each cDNA was diluted ¼ and aliquots were stored at −20° C. until the PCR reactions were carried out.

Real-time RT-PCR was performed for two reference genes: 18S ribosomal RNA (18S rRNA), glyceraldehyde-3-phosphate dehydrogenase (GAPDH); and eleven target genes: alkaline phosphathase (ALP), Interleukin 6 (IL-6), Collagen (Coll-1), Osteocalcin (OC), Bone Morphogenetic Protein 2 (BMP-2), Osterix (Osx), Receptor activator of nuclear factor kappa-B ligand (RANKL), Osteoprogesterin (OPG) and genes involved in vitamin D synthesis such as Vitamin $D_3$ 25-hydroxylase (CYP27A1) and 25 hydroxyvitamin $D_3$-1-alpha hydroxylase (CYP27B1). Real-time PCR were performed in the Lightcycler 480® (Roche Diagnostics, Germany). Each reaction contained 5 μl of LightCycler-FastStart DNA Master$^{PLUS}$ SYBR Green I (Roche Diagnostics, Mannheim, Germany), 0.5 μM of the sense and antisense specific primers (Table 1) and 3 μl of the cDNA dilution in a final volume of 10 μl. The normal amplification program consisted of a preincubation step for denaturation of the template cDNA (10 min 95° C.), followed by 45 cycles consisting of a denaturation step (10 s 95° C.), an annealing step (10 s 60° C., except for ALP that was 10 s at 65° C., OSX with 10 s at 68° C.) and an extension step (10 s 72° C.). After each cycle, fluorescence was measured at 72° C. Every run included a negative control without cDNA template. To confirm amplification specificity, PCR products were subjected to a melting curve analysis on the LightCycler and subsequently 2% agarose/TAE gel electrophoresis, Tm and amplicon size, respectively.

To allow relative quantification after PCR, real-time efficiencies were calculated from the given slopes in the LightCycler 480 software (Roche Diagnostics, Mannheim, Germany) using serial dilutions. Relative quantification after PCR was calculated by normalizing target gene concentration in each sample by the concentration mean of the two reference genes in given sample using the Advanced relative quantification method provided by the LightCycler 480 analysis software.

3.10. ALP Activity, Calcium Content and Total Protein Determination

Cell monolayer was collected at 21 cell differentiation days and PBS 0.1% Triton X-100 was added to solubilize proteins. Cell lysates were put into freeze/thaw cycles (liquid nitrogen and 37° C. water bath) to improve protein recovery. After centrifugation at 33,000 g for 15 min at 4° C., supernatants acquired were assayed for ALP activity, calcium content and total protein determination. ALP activity was calculated by measuring the cleavage of p-Nitrophenyl Phosphate (pNPP) (Sigma, St. Louis, Mo., USA) in a soluble yellow end product which absorbs at 405 nm. A volume of 100 μl of this substrate was used in combination with 25 μl of each sample supernatant or standard point. The standard curve was prepared from calf intestinal alkaline phosphatase (CIAP, 1 U/μl) (Promega, Madison, Wis., USA) by mixing 1 μl from the stock CIAP with 5 ml of alkaline phosphatase buffer (1:5000 dilution), and then making 1:5 serial dilutions. Once the reaction was carried out, after 30 min in dark at room temperature, it was stopped with the addition of 50 μl of 3 M sodium hydroxide. At this point, absorbance was read at 405 nm.

To determine calcium content samples were analyzed by inductively coupled plasma atomic emission spectrometry (Optima 5300 DV, PerkinElmer, Massachussetts, USA). Cell supernatants were diluted 1:1 in 0.5N HCl to extract calcium. Data were compared to $CaCl_2$ standard curve included in the assay.

Total protein was determined using a BCA protein assay kit (Pierce, Rockford, Ill., USA). For the analysis, cell supernatants were diluted 1:1 in PBS 0.1% Triton X-100. Standard curve and samples were analyzed as described by the manufacturer and reading the absorbance at 562 nm.

3.11. Statistics

All data are presented as mean values ±standard error of the mean (SEM). Statistical differences between groups were determined by Mann-Whitney-test or by Student t-test depending on their normal distribution. The SPSS® program for Windows, version 17.0 was used. Results were considered statistically significant at the p-values ≤0.05.

3.12. Results a) Changes in Chemical Structure of 7-DHC after UV Exposure and $D_3$ on Coated Titanium Implants The absorbance spectra of 7-DHC changed with UV irradiation time (Table 2, FIG. 10), starting from short UV irradiation times of 15 min. From the absorbance spectra and the changes of peak areas measured (Table 2, FIG. 10), can be assumed that no —OH groups were generated due to the irradiation, as the —OH stretch absorbance at 3300 $cm^{-1}$ decreased slightly in area and also the absorbances of the –OH deformation vibration and —C—O stretch typical for phenolic compounds at 1360 $cm^{-1}$ and 1220 $cm^{-1}$ did not change in intensity (data not shown). A peak shift of the –OH stretching vibration towards higher wavenumbers for irradiated 7-DHC suggested the appearance of an additional peak at about 3470 $cm^{-1}$ (FIG. 10) that can be assigned to –C═O stretching vibrations. Further, the –C═O stretching vibrations of ester and carboxylic groups at 1716 $cm^{-1}$ increased clearly with irradiation time (Table 2) and may be caused by photooxidation processes. Peak fitting of the absorbance peak at 1850 $cm^{-1}$ to 1550 $cm^{-1}$ (FIG. 10) revealed the appearance of trans C═C bonds (1680 $cm^{-1}$) with an increasing peak area with irradiation time. The peak area of cis C═C double bonds (1650 $cm^{-1}$) increased as well, while the area of the C═C aromatic bonds (1625 $cm^{-1}$) remained stable (Table 2). In addition, changes in the region 970 $cm^{-1}$ to about 500 $cm^{-1}$ indicated changes in the ring substitution pattern, namely an increase for absorbances commonly assigned to 1,2,3 trisubstituted benzenes (960 $cm^{-1}$, 890 $cm^{-1}$, 800 $cm^{-1}$), and decreased absorbances for pentasubstituted benzenes (880 $cm^{-1}$) and 1,2,4,5 tetrasubstituted benzene (865 $cm^{-1}$) (FIG. 11). Thus, the FTIR spectra showed signs for changes in the ring structure, which are indicative of the ring opening reaction that converts 7-DHC to previtamin $D_3$.

TABLE 2

Quantification of the absorbance peak between 3800 $cm^{-1}$ and 2700 $cm^{-1}$ and of some absorbance peaks between 1850 $cm^{-1}$ and 1550 $cm^{-1}$. The assigned molecular group with the approximate wavenumber of the maximum absorbance is given.

| Substance | Peak area/A cm−1 | | | | | |
| --- | --- | --- | --- | --- | --- | --- |
| | C═O 3470 $cm^{-1}$ | OH 3300 $cm^{-1}$ | C═O 1716 $cm^{-1}$ | trans C═C 1680 $cm^{-1}$ | cis C═C 1650 $cm^{-1}$ | C═C aromatic 1625 $cm^{-1}$ |
| Cholecalciferol | — | 59.7 | 0.2 | 0.1 | 1.0 | 1.1 |
| 7-DHC | — | 136.8 | 4.3 | 0.3 | 2.3 | 0.5 |
| 15 min UV | 34.4 | 107.7 | 5.5 | 2.9 | 9.4 | 0.5 |
| 30 min UV | 22.3 | 98.8 | 8.2 | 1.0 | 10.4 | 0.4 |
| 60 min UV | 27.9 | 93.3 | 23.3 | 9.5 | 8.2 | 1.3 | b) Effect of UV Time Exposure of 7-DHC Coated Titanium Implants on Cell Viability In Example 2, it has been showed that 0.2 nmols was the optimal amount of 7-DHC to be used in polystyrene TCP under UV irradiation for the production of active vitamin D in MC3T3-E1 osteoblasts. The same amount of 7-DHC was applied on the surface of Ti disks in the present study, as the culture plates containing the titanium disks had the same surface area as the previously used. The effect of different UV irradiation times of 7-DHC coated titanium implants on MC3T3-E1 cell viability after 24 h, and compared to control surfaces (treated with ethanol only) under the same UV irradiation conditions was investigated. As seen in FIG. 12, UV exposure increased cell viability for the ethanol treatment. Furthermore, protective effects were found in ethanol group from 0 to 15 minutes of UV irradiation compared to negative control (TCP), but also in 7-DHC samples previously UV-activated from 5 to 10 minutes. Significant differences were also observed for the 7-DHC group compared to their ethanol control group, after 15 min of UV irradiation.

c) Effect of UV Time Exposure of 7-DHC Coated Titanium Implants on Cell Number and Cell Covered Surface Images obtained from confocal and SEM microscopes show the cell morphology and cell number for different UV-exposure times of 7-DHC and ethanol treatments on Ti surfaces (FIG. 13). It can be observed from the pictures that more cells were present after 30 minutes of UV irradiation for both 7-DHC and ethanol groups. Data obtained from DNA content confirmed the significantly higher amount of cells in these groups. In addition, 7-DHC samples exposed during 30 minutes of UV irradiation revealed a significant greatest percentage of implant surface covered with cells compared to surfaces treated with 7-DHC without irradiation. Together with the LDH activity results, the cell morphology and cell number confirmed the biocompatibility of the treatments and conditions used for the studies.

d) Effect of UV Time Exposure of 7-DHC Coated Titanium Implants on 25-$D_3$ Secretion and Gene Expression of Hydroxylase Enzymes The secretion of 25-$D_3$ to the cell culture media after 48 h was analyzed for the different UV irradiation time conditions (FIG. 14). Only 25-$D_3$ was analyzed in the samples because its reported longer half-life and higher concentration than 1,25-$D_3$ and cholecalciferol. As seen in FIG. 14, significant differences between 7-DHC and ethanol-treated Ti samples when UV exposure time was 15 minutes were detected. Also significantly different was the amount of 25-$D_3$ released from 7-DHC UV-treated vs. UV-untreated. Surprisingly, UV irradiation of ethanol-treated Ti samples showed a time-dependent increase in the release of 25-$D_3$, although this was not significant and in a minor extent than 7-DHC-treated samples, except for the group UV irradiated for 30 min.

The gene expression of the hydroxylase CYP27A1 mRNA in 7-DHC samples (FIG. 15A) revealed a trend to increase its gene expression with the UV irradiation time, with a maximum after 15 min. Significant differences were found at 10 and 30 min of UV exposure compared to 7-DHC UV-untreated samples and at 30 min compared to ethanol-treated samples at the same UV-irradiation time. On the other hand, CYP27B1 gene expression was also upregulated when increasing UV exposure time in 7-DHC samples (FIG. 16B) with significant results compared to UV-untreated 7DHC samples at 15 and 30 min, whereas ethanol treated samples kept a steady gene expression level, but with significant differences compared to UV-untreated samples were at 5 and 15 minutes of UV irradiation.

e) Effect of UV Time Exposure of 7-DHC Coated Titanium Implants on Osteoblast Differentiation Next, gene expression of several markers related to proliferative stage of osteoblasts (collagen type-1), matrix maturation and differentiation (ALP, BMP-2, osterix), mineralization (osteocalcin) and cytokines (IL-6, RANKL, OPG) was analyzed to investigate the effect of UV time exposure of 7-DHC coated titanium implants on MC3T3-E1 osteoblasts (FIG. 16). Collagen type-1 revealed a trend to decrease its gene expression with UV exposure time (FIG. 16A) and significant differences were found in 7-DHC samples exposed during 15 and 30 minutes of UV irradiation compared to ethanol-treated samples and UV-untreated 7-DHC samples. As regards to ALP mRNA levels (FIG. 16B), statistical differences were reached for 30 minutes UV-exposed 7-DHC group compared to ethanol UV-exposed group, although all the groups treated with 7-DHC and UV irradiation displayed higher ALP mRNA levels than their ethanol and UV-treated groups. OSX mRNA levels were very similar between all the groups (FIG. 16C), only significant differences were found at 10 minutes of UV exposure. OC gene expression was similar between different UV exposure times among the groups (FIG. 16D), although significant differences were found in control group irradiated during 15 minutes when compared to non-irradiated one. A tendency to increased OC mRNA levels in the 7-DHC UV-exposed for 15 min was observed. No statistical differences were observed for BMP-2 and IL-6 mRNA levels when exposed to UV (FIGS. 16E and 16F). However, RANKL mRNA levels revealed a statistical significant increase for 10 minutes UV-exposed 7-DHC group compared to ethanol and a significant decrease for 30 minutes UV-exposed 7-DHC samples (FIG. 16G). Meanwhile, OPG mRNA levels kept a steady expression for the different UV exposure times (FIG. 16H), only a decrease was found for the 30 min UV-exposed 7-DHC samples.

In order to verify the effect of 7-DHC treatment on RANKL gene expression, it was analyzed different 7-DHC concentrations ($2\times10^{-2}$ nmols, 0.2 nmols and 2 nmols) that were UV-treated and UV-untreated for 15 minutes and compared to the treatment with $D_3$ and 25-$D_3$ which do not need UV-activation (FIG. 17). Statistical significances were found in all 7-DHC UV-treated groups and also for $2\times10^{-2}$ nmols $D_3$ treatment when compared to control. Furthermore, $2\times10^{-2}$ nmols and 0.2 nmols 7-DHC groups revealed a significant decrease in RANKL mRNA expression when were exposed to UV light unlike no UV-untreated 7-DHC groups which expressed higher relative RANKL levels. Similar to the previous results in FIG. 16H, OPG mRNA levels were kept quite similar between different samples (data not shown).

f) Effect of UV Time Exposure of 7-DHC Coated Titanium Implants on Alkaline Phosphatase (ALP) Activity and Mineralization To achieve the effect of treatments on MC3T3-E1 differentiation, ALP activity was measured in the cell monolayer on day 21 after cell culturing. UV-treated 7-DHC cells induced a significant higher ALP activity than the 7-DHC UV-untreated group (FIG. 18A). Additionally, 7-DHC and $D_3$ UV-untreated groups (44.75±3.50% and 35.28±4.23% respectively) showed statistically lower ALP activity than ethanol UV-untreated group, and 25-$D_3$ UV-untreated group showed similar ALP activity (77.40±13.40%) than the ethanol control. Calcium levels were measured at 28 days of cell differentiation by inductively coupled plasma atomic emission spectrometer (ICP-AES). MC3T3-E1 cells showed a significant increase of the calcium content in UV-treated 7-DHC group compared to the UV-untreated cells and control group (FIG. 18B). Only a trend to increased calcium levels was also observed for 25-$D_3$ group, while for $D_3$ group was similar to 7-DHC UV-untreated group (data not shown).

3.13 Conclusion

No cytotoxic effect was found for Ti implants that were treated with 7-DHC and UV-irradiated. Moreover, Ti implants that were treated with 7-DHC and UV-irradiated for 15 min showed increased 25-hydroxyvitamin $D_3$ (25-$D_3$) production, together with increased ALP activity, calcium content and gene expression of several osteoblast markers. Interestingly, RANKL gene expression was significantly reduced in osteoblasts cultured on Ti implants with 7-DHC and UV-irradiated. In conclusion, these findings demonstrate for the first time that UV-activated 7-DHC is a biocompatible coating of Ti implants, which allows the osteoblastic cells to produce themselves active vitamin D, with demonstrated positive effects on osteoblast differentiation in vitro.

Example 4

Effect of Antioxidant Vitamin E on the Conversion Efficiency of 7-DHC to Vitamin $D_3$ in Polymeric and Titanium Surfaces by UV Irradiation The effect of vitamin E on the conversion efficiency of 7-dehydrocholesterol (7-DHC) to vitamin $D_3$ by UV irradiation at 302 nm was evaluated both in plastic and titanium surfaces coated with 7-DHC.

4.1. Materials, Methods, and Equipment

Substrates (polystyrene, 96 well plate; or titanium, polished titanium disks, 6.2 mm diameter, 2 mm height, inserted in a 96 well plate) were covered with 0.2 nmol of 7-DHC and Vitamin E (7-DHC: VitE=20:1, m:m) by dropping 10 μl of a 7-DHC/VitE solution in absolute ethanol. After leaving the solvent to evaporate for 15 min, samples were UV irradiated for 15 min at 302 nm. The amounts of 7-DHC and $D_3$ present in the surfaces were quantified by HPLC. Results were compared with substrates without Vit E and with non-irradiated surfaces. Pure ethanol was used as control for all groups. Sunlight exposure was avoided for all surfaces.

4.2. HPLC Analysis a) Reagents and Standards

All solvents used were HPLC or analytical grade. Methanol (HPLC gradient grade), acetonitrile and tetrahydrofurane (both HPLC grade) were purchased from Fisher Scientific. High purity deionized Milli-Q water was obtained from a Millipore system. Absolute Ethanol was purchased from Scharlau. 7-dehydrocholesterol, Vitamin $D_3$ and Vitamin E were purchased from Sigma-Aldrich.

Individual stock standard solutions of 7-DHC (250 µg/ml), Vitamin $D_3$ (10 mg/ml) and Vitamin E (1 mg/ml) were prepared in methanol and stored at −20° C. Standard solutions of lower concentrations were obtained by dilution of stock solutions in methanol.

b) Sample Preparation

The coating of each surface was extracted by adding 100 µl of 'methanol/acetonitrile/tetrahydrofurane/water' (67:16:2:15, v:v) to each well and shaking the plate for 2 min at 20 rpm. The content of three replicate wells was mixed to give a sample of ≈300 µl. An aliquot of 100 µl of the sample was injected in the HPLC system. Two replicate samples were prepared and analyzed for each group.

b) Instrumentation

The analysis were carried out using a Waters liquid chromatographic system (Milford, Mass., USA), equipped with a refrigerated automatic injector WISP700 and a 600 pump system, connected to a Waters 996 photodiode array (PDA) detector. The software Empower was used for instrument control and data analysis. Detection was carried out at 282 nm.

c) Cromatographic Conditions

A Nova Pak C18 column (Waters) was used to separate sample components before detection. The column temperature was set to 30° C. Two solvents, A: 'methanol/acetonitrile/tetrahydrofurane/water (67:16:2:15, v:v), and B: 'methanol/acetonitrile/tetrahydrofurane' (75:20:5, v:v) were used in gradient elution mode as the mobile phase. Solvents A and B were vacuum-filtered through a Nylon membrane (0.45 µm pore diameter) and degassed before use. The mobile phase flow rate was 1 ml·min$^{-1}$. The binary gradient used was as follows: from 5% B to 90% B in three minutes, held for 9.5 min at 90% B, from 90% B to 5% B in one minute and equilibrated between injections at the initial conditions for 5 min (total run time=15 min+5 min equilibration between injections).

d) Quantification of Analytes

Quantification was performed by integration of the peak area of the corresponding analyte and interpolation of the peak area in 7-DHC or Vit $D_3$ standard curves. At the working concentrations used, Vitamin E was not detectable and did not interfere with the quantification of the analytes Vit $D_3$ and 7-DHC.

4.3. Results

Concentration of 7-DHC solutions ($C_{7-DHC}$) in ethanol used in the experiments to coat the substrates was determined by HPLC in order to determine the real amount of 7-DHC added to each sample) ($m_{7-DHC}^0$). Results are shown in Table 3.

TABLE 3

Concentration of 7-DHC and 7-DHC + Vit E working solutions ($C_{7-DHC}$) and amount of 7-DHC coating each substrate sample ($m_{7-DHC}^0$) determined by HPLC.

| Experiment | Working solution | $C_{7-DHC}$ HPLC ng·µl$^{-1}$ | $m_{7-DHC}^0$ ng/well |
|---|---|---|---|
| Polystyrene | 7-DHC | 10.2 | 102 |
|  | 7-DHC + Vit E | 9.6 | 96 |
| Titanium | 7-DHC | 10.9 | 109 |
|  | 7-DHC + Vit E | 10.7 | 107 |

Table 4 shows the amounts of Vitamin $D_3$ ($m_{D3}$) and 7-DHC ($m_{7-DHC}$) quantified by HPLC before and after UV irradiation, and Vitamin $D_3$ product yields ($\eta_{D3}$) reached for each group.

TABLE 4

Effect of Vitamin E on the conversion efficiency of 7-DHC to Vitamin $D_3$ by UV irradiation of 7-DHC in plastic and titanium substrates. Values obtained by HPLC from two sample replicates.

| Substrate | Treatment[a] |  | $m_{7-DHC}$ ng/well | $m_{D3}$ ng/well | $m_{7-DHC}$ (%)[b] | $\eta_{D3}$ (%)[c] |
|---|---|---|---|---|---|---|
| Polystyrene | Non irradiated | 7-DHC | 90.1 ± 2.9 | — | 88 | — |
|  |  | 7-DHC + Vit E | 84.8 ± 10.2 | — | 88 | — |
|  | Irradiated | 7-DHC | 29.2 ± 2.0 | 11.8 ± 0.4 | 29 | 13.1 ± 0.4 |
|  |  | 7-DHC + Vit E | 30.0 ± 2.3 | 17.2 ± 0.8 | 31 | 20.3 ± 1.0 |
| Titanium | Non irradiated | 7-DHC | 99.9 ± 3.0 | — | 92 | — |
|  |  | 7-DHC + Vit E | 96.7 ± 2.0 | — | 90 | — |
|  | Irradiated | 7-DHC | 42.1 ± 3.4 | 16.4 ± 0.7 | 39 | 16.4 ± 0.7 |
|  |  | 7-DHC + Vit E | 49.7 ± 1.0 | 20.5 ± 3.1 | 46 | 20.5 ± 3.1 |

[a]10 µl of stock solutions were added to each substrate. HPLC concentrations of stock solutions are shown in Table 3. Irradiated samples were exposed to UV light (λ = 302 nm) for 15 min. Non irradiated samples were protected from sunlight.
[b]$m_{7-DHC}$ (%) = 100* $m_{7-DHC}/m_{7-DHC}^0$; $m_{7-DHC}^0$: initial mass of 7-DHC added to each well, calculated from HPLC stock concentrations (see Table 3).
[c]Vit $D_3$ product yield: percentage of moles of Vit $D_3$ detected after UV irradation in relation to moles of 7-DHC detected before irradiation. Theoretical yield: 1 mol 7-DHC = 1 mol $D_3$. $\eta_{D3}$ = 100* $n_{D3}/n_{7-DHC}$;

Values of Table 4 show that the amount of 7-DHC recovered and quantified from non-irradiated substrates analyzed by HPLC is similar for all samples (88-92% vs. the initially added amount $m_{7-DHC}^0$), with and without Vit E, both for plastic and titanium substrates. FIG. 19 shows one of the chromatograms obtained for non-irradiated samples.

After UV irradiation, $D_3$ was produced and detected in all samples. Formation of lumisterol and other reaction by-products like tachysterol were also detected by HPLC (FIGS. 20 and 21). As Table 4 shows, samples with Vitamin E presented a higher amount of $D_3$ after irradiation (17.2 ng/well in plastic substrates, 20.5 ng/well in titanium) than samples without Vit E (11.8 ng/well in plastic substrates, 16.4 ng/well in titanium). The amounts of 7-DHC detected after irradiation decreased from 88-92% to 29-46%, without differences for Vit E-treated and no treated groups.

The conversion of 7-DHC to Vit D$_3$ was significantly higher for the Vit E groups (20.3% in plastic substrates, 20.5% in titanium) compared to groups without Vit E (13.1% in plastic, 16.4% in titanium).

4.4. Conclusion

When using combinations of 7-DHC with vitamin E, as shown in the Examples, there is a more efficient conversion from 7-DHC to cholecalciferol after UV-irradiation, not by doing the expected function to prevent its oxidation (since the remaining amount of 7-DHC after UV-irradiation was the same as the initial) but by enhancing its conversion rate, showing then an unexpected interaction of 7-DHC with vitamin E when given together on the surface of the implants.

TABLE 5

Primer sequences used for real time RT-PCR. Primer sequences for target and reference genes, product size, and accession number are shown.

| Name | 5'-Sequence-3' | Product size | Accession number |
| --- | --- | --- | --- |
| Osteocalcin | S: CCG GGA GCA GTG TGA GCT TA<br>AS: TAG ATG CGT TTG TAG GCG GTC | 81 bp | NM_007541 |
| Collagen-I | S: AGA GCA TGA CCG ATG GAT TC<br>AS: CCT TCT TGA GGT TGC CAG TC | 177 bp | NM_007742.3 |
| Interleukin-6 | S: ACT TCC ATC CAG TTG CCT TC<br>AS: TTT CCA CGA TTT CCC AGA GA | 171 bp | NM_031168.1 |
| ALP | S: AAC CCA GAC ACA AGC ATT CC<br>AS: GAG AGC GAA GGG TCA GTC AG | 151 bp | X13409 |
| BMP-2 | S: GCT CCA CAA ACG AGA AAA GC<br>AS: AGC AAG GGG AAA AGG ACA CT | 178 bp | NM_007553.2 |
| Osterix | S: ACT GGC TAG GTG GTG GTC AG<br>AS: GGT AGG GAG CTG GGT TAA GG | 135 bp | NM_007419 |
| RANKL | S: GGC CAC AGC GCT TCT CAG<br>AS: TGA CTT TAT GGG AAC CCG AT | 141 bp | NM_011613 |
| OPG | S: AGA CCA TGA GGT TCC TGC AC<br>AS: AAA CAG CCC AGT GAC CAT TC | 131 bp | NM_008764.3 |
| CYP27A1 | S: CGT CCT CTG CTG CCC TTT GG AAG<br>AS: GTG TGT TGG ATG TCG TGT CCA CCC | 247 bp | NM_024264.4 |
| CYP27B1 | S: TCC TGT GCC CAC CCC CAT GG<br>AS: AGG GAG ACT AGC GTA TCT TGG GGA | 167 bp | NM_010009.2 |
| CYP24A1 | S: CTA TCG GGA CCA TCG CAA CGA AGC<br>S: GCC CCA TAA AAT CAG CCA AGA CCT CA | 158 bp | NM_009996.3 |
| GAPDH | ACC CAG AAG ACT GTG GAT GG<br>CAC ATT GGG GGT AGG AAC AC | 171 bp | XM_132897 |
| 18S rRNA | S: GTA ACC CGT TGA ACC CCA TT<br>AS: CCA TCC AAT CGG TAG TAG CG | 151 bp | X00686 |

What is claimed is:

1. An implant comprising a metallic or polymeric base partially or totally coated with cholecalciferol; wherein the concentration of cholecalciferol in the coating is between 1 fmol/mm$^2$ and 5 nmol/mm$^2$.

2. The implant according to claim 1, wherein said base has been previously coated with 7-dehydrocholesterol and irradiated with UV light to induce the formation of cholecalciferol.

3. The implant according to claim 1, wherein the concentration of cholecalciferol in the coating is between 0.1 and 5 pmol/mm$^2$.

4. The implant according to claim 1, wherein the metallic or polymeric base is a metallic base comprising a metal, metal alloy, metal oxide, or combinations thereof.

5. The implant according to claim 4, wherein the metallic base comprises metallic titanium, a titanium alloy, a titanium oxide, or combinations thereof.

6. The implant according to claim 5, wherein the metallic base comprises at least 90% by weight of titanium.

7. The implant according to claim 4, wherein said metallic base comprises a metal selected from the group consisting of titanium, zirconium, tantalum, hafnium, niobium, chromium, vanadium and stainless steel.

8. The implant according to claim 1, wherein the metallic or polymeric base is a polymeric base comprising polystyrene, polyurethane or combinations thereof.

9. The implant according to claim 1, wherein the implant is selected from the group consisting of a surgical implant, an orthopedic implant, a dental implant, an orthopedic fixation device, an orthopedic joint replacement, a prosthetic disc for spinal fixation, or a graft material.

10. The implant according to claim 1 further comprising an antioxidant selected from a vitamin E compound, vitamin C, vitamin A, lycopene, lutein, beta-carotene, alpha-carotene, zeaxanthin, selenium, zinc, coenzyme-Q10, catechins, resveratrol, proanthocyanidins, genistein, and daidzein.

11. The implant according to claim 10, wherein the antioxidant is a vitamin E compound comprising one or more of alpha-tocopherol, beta-tocopherol, delta-tocopherol, gamma-tocopherol, alphatocotrienol, beta-tocotrienol, delta-tocotrienol, gamma-tocotrienol, alpha-tocopherol acetate, beta-5 tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta-tocotrienol succinate, delta-tocotrienol succinate, gamma-tocotrienol succinate, vitamin E TPGS, mixed tocopherols, derivatives, analogs and pharmaceutically acceptable salts thereof.

\* \* \* \* \*